US009033920B2

(12) United States Patent
Miesel

(10) Patent No.: US 9,033,920 B2
(45) Date of Patent: May 19, 2015

(54) DETERMINING CATHETER STATUS

(75) Inventor: Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 978 days.

(21) Appl. No.: 12/721,647

(22) Filed: Mar. 11, 2010

(65) Prior Publication Data

US 2010/0168607 A1  Jul. 1, 2010

Related U.S. Application Data

(63) Continuation-in-part of application No. 12/623,484, filed on Nov. 23, 2009, and a continuation-in-part of application No. 11/731,356, filed on Mar. 30, 2007, now Pat. No. 8,323,244, and a continuation-in-part of (Continued)

(51) Int. Cl.
*A61M 5/00* (2006.01)
*A61M 5/142* (2006.01)
*A61M 5/168* (2006.01)
*A61M 27/00* (2006.01)
*A61M 5/172* (2006.01)

(52) U.S. Cl.
CPC ....... *A61M 5/14276* (2013.01); *A61M 5/16859* (2013.01); *A61M 27/006* (2013.01); *A61M 2005/1726* (2013.01); *A61M 2202/0464* (2013.01)

(58) Field of Classification Search
USPC .......................... 604/131, 65, 67, 891.1, 111
See application file for complete search history.

(56) References Cited

U.S. PATENT DOCUMENTS

| 3,882,443 | A | 5/1975 | Mortia |
| 4,137,913 | A | 2/1979 | Georgi |
| 4,373,527 | A | 2/1983 | Fischell |
| 4,388,833 | A | 6/1983 | Kuwayama |
| 4,530,696 | A | 7/1985 | Bisera |

(Continued)

FOREIGN PATENT DOCUMENTS

| EP | 0 248 632 | 12/1987 |
| EP | 0 248 633 | 12/1987 |

(Continued)

OTHER PUBLICATIONS

Giepel et al., "Design of an Implantable Active Microport System for Patient Specific Drug Release", Proceedings of the 24$^{th}$ IASTED International Mutli-Conference on Biomedical Engineering (The International Association of Science and Technology for Development), Feb. 15-17, 2006, Innsbruck, Austria; pp. 161-166.

(Continued)

*Primary Examiner* — Nicholas Lucchesi
*Assistant Examiner* — Diva K Chander
(74) *Attorney, Agent, or Firm* — Mueting, Raasch & Gebhardt, P.A.

(57) ABSTRACT

A method for monitoring the status of an implanted catheter includes monitoring changes in pressure within a lumen of a catheter associated with physiological parameters ("physiological pressure") and changes in pressure within the lumen of the catheter associated with bolus infusion of fluid into the catheter or bolus withdrawal of infusion from the catheter ("bolus pressure"). Methods that employ monitoring both physiological pressure and bolus pressure can provide information that cannot be obtained from monitoring physiological pressure or bolus pressure alone.

13 Claims, 16 Drawing Sheets

Related U.S. Application Data application No. 11/731,355, filed on Mar. 30, 2007, now Pat. No. 8,317,770, and a continuation-in-part of application No. 11/778,400, filed on Jul. 16, 2007, now Pat. No. 7,955,319, which is a continuation of application No. 10/836,115, filed on Apr. 30, 2004, now Pat. No. 7,320,676.

(60) Provisional application No. 60/789,729, filed on Apr. 6, 2006, provisional application No. 60/508,020, filed on Oct. 2, 2003.

(56) References Cited

U.S. PATENT DOCUMENTS

| | | | | |
|---|---|---|---|---|
| 4,534,756 | A | 8/1985 | Nelson | |
| 4,551,133 | A | 11/1985 | Zegers de Beyl | |
| 4,619,653 | A | 10/1986 | Fischell | |
| 4,710,163 | A | 12/1987 | Butterfield | |
| 4,714,462 | A | 12/1987 | DiDomenico | |
| 4,784,645 | A | 11/1988 | Fischell | |
| 4,979,940 | A | 12/1990 | Bobo, Jr. | |
| 5,006,997 | A | 4/1991 | Reich | |
| 5,024,668 | A | 6/1991 | Peters | |
| 5,040,536 | A | 8/1991 | Riff | |
| 5,059,171 | A | 10/1991 | Bridge | |
| 5,078,682 | A | 1/1992 | Miki | |
| 5,087,245 | A | 2/1992 | Doan | |
| 5,096,385 | A | 3/1992 | Georgi | |
| 5,116,203 | A * | 5/1992 | Natwick et al. | 417/53 |
| 5,158,547 | A | 10/1992 | Doan | |
| 5,176,631 | A | 1/1993 | Koenig | |
| 5,190,522 | A | 3/1993 | Wojcicki | |
| 5,205,819 | A | 4/1993 | Ross | |
| 5,207,666 | A | 5/1993 | Idriss | |
| 5,219,279 | A * | 6/1993 | Natwick et al. | 417/479 |
| 5,276,610 | A | 1/1994 | Maeda | |
| 5,279,544 | A | 1/1994 | Gross | |
| 5,290,231 | A | 3/1994 | Marcadis | |
| 5,328,460 | A | 7/1994 | Lord | |
| 5,336,181 | A | 8/1994 | Nakao | |
| 5,342,298 | A | 8/1994 | Michaels | |
| 5,356,378 | A | 10/1994 | Doan | |
| 5,496,273 | A | 3/1996 | Pastrone | |
| 5,501,665 | A | 3/1996 | Jhuboo | |
| 5,535,752 | A | 7/1996 | Halperin | |
| 5,560,366 | A | 10/1996 | Harada | |
| 5,605,545 | A | 2/1997 | Nowosielski | |
| 5,609,576 | A | 3/1997 | Voss | |
| 5,645,734 | A | 7/1997 | Kenley | |
| 5,669,877 | A | 9/1997 | Blomquist | |
| 5,695,473 | A | 12/1997 | Olsen | |
| 5,800,387 | A | 9/1998 | Duffy | |
| 5,827,223 | A | 10/1998 | Butterfield | |
| 5,853,386 | A | 12/1998 | Davis | |
| 5,893,838 | A | 4/1999 | Daoud | |
| 5,899,873 | A | 5/1999 | Jones | |
| 5,906,589 | A | 5/1999 | Gordon | |
| 5,928,195 | A | 7/1999 | Malamud | |
| 5,935,106 | A | 8/1999 | Olsen | |
| 6,152,898 | A | 11/2000 | Olsen | |
| 6,203,523 | B1 | 3/2001 | Haller | |
| 6,213,972 | B1 | 4/2001 | Butterfield | |
| 6,241,704 | B1 | 6/2001 | Peterson | |
| 6,358,225 | B1 | 3/2002 | Butterfield | |
| 6,364,842 | B1 | 4/2002 | Amano | |
| 6,394,986 | B1 | 5/2002 | Millar | |
| 6,423,029 | B1 | 7/2002 | Elsberry | |
| 6,423,035 | B1 | 7/2002 | Das | |
| 6,458,102 | B1 | 10/2002 | Mann | |
| 6,464,687 | B1 | 10/2002 | Ishikawa | |
| 6,485,465 | B2 | 11/2002 | Moberg | |
| 6,551,290 | B1 | 4/2003 | Elsberry | |
| 6,609,071 | B2 | 8/2003 | Shapiro | |
| 6,620,151 | B2 | 9/2003 | Blischak | |
| 6,648,821 | B2 | 11/2003 | Lebel | |
| 6,716,193 | B1 | 4/2004 | Neftel | |
| 6,740,059 | B2 | 5/2004 | Flaherty | |
| 6,742,999 | B1 | 6/2004 | Nusser | |
| 6,966,325 | B2 | 11/2005 | Erickson | |
| 7,022,116 | B2 | 4/2006 | Morris | |
| 7,054,782 | B2 | 5/2006 | Hartlaub | |
| 7,092,797 | B2 | 8/2006 | Gaines | |
| 7,104,763 | B2 | 9/2006 | Bouton | |
| 7,118,565 | B2 | 10/2006 | Abboud | |
| 7,255,680 | B1 * | 8/2007 | Gharib | 604/67 |
| 7,255,683 | B2 | 8/2007 | Vanderveen | |
| 7,291,126 | B2 | 11/2007 | Shekalim | |
| 7,311,693 | B2 | 12/2007 | Shekalim | |
| 7,320,676 | B2 | 1/2008 | Miesel | |
| 7,338,464 | B2 | 3/2008 | Blischak | |
| 7,437,644 | B2 | 10/2008 | Ginggen | |
| 7,452,190 | B2 | 11/2008 | Bouton | |
| 7,505,869 | B2 | 3/2009 | Hartlaub | |
| 7,621,878 | B2 | 11/2009 | Ericson | |
| 7,722,574 | B2 | 5/2010 | Toman | |
| 7,998,111 | B2 | 8/2011 | Moberg | |
| 2001/0034502 | A1 | 10/2001 | Moberg | |
| 2002/0040208 | A1 | 4/2002 | Flaherty | |
| 2002/0065471 | A1 | 5/2002 | Amano | |
| 2002/0072733 | A1 | 6/2002 | Flaherty | |
| 2002/0077581 | A1 | 6/2002 | Davidner | |
| 2002/0087115 | A1 | 7/2002 | Hartlaub | |
| 2002/0107477 | A1 | 8/2002 | Kipfer | |
| 2002/0120236 | A1 | 8/2002 | Diaz | |
| 2002/0173773 | A1 | 11/2002 | Olsen | |
| 2003/0073954 | A1 | 4/2003 | Moberg | |
| 2003/0078547 | A1 | 4/2003 | Shekalim | |
| 2003/0088238 | A1 | 5/2003 | Poulsen | |
| 2003/0125662 | A1 | 7/2003 | Bui | |
| 2003/0135154 | A1 | 7/2003 | Heiniger | |
| 2003/0236489 | A1 | 12/2003 | Jacobson | |
| 2004/0034331 | A1 | 2/2004 | Toman | |
| 2004/0044305 | A1 | 3/2004 | Hughett | |
| 2004/0085215 | A1 | 5/2004 | Moberg | |
| 2004/0087894 | A1 | 5/2004 | Flaherty | |
| 2004/0127844 | A1 | 7/2004 | Flaherty | |
| 2004/0220548 | A1 | 11/2004 | Heruth | |
| 2004/0230125 | A1 | 11/2004 | Amano | |
| 2004/0260233 | A1 | 12/2004 | Garibotto | |
| 2004/0260234 | A1 | 12/2004 | Srinivasan | |
| 2005/0075624 | A1 | 4/2005 | Miesel | |
| 2005/0090799 | A1 | 4/2005 | Morris | |
| 2005/0123420 | A1 | 6/2005 | Richter | |
| 2005/0148885 | A1 | 7/2005 | Tweed | |
| 2005/0192529 | A1 | 9/2005 | Butterfield | |
| 2005/0209512 | A1 | 9/2005 | Heruth | |
| 2005/0209513 | A1 | 9/2005 | Heruth | |
| 2005/0222643 | A1 | 10/2005 | Heruth | |
| 2005/0234514 | A1 | 10/2005 | Heruth | |
| 2005/0234518 | A1 | 10/2005 | Heruth | |
| 2005/0241387 | A1 | 11/2005 | Miesel | |
| 2005/0245858 | A1 | 11/2005 | Miesel | |
| 2005/0267413 | A1 | 12/2005 | Wang | |
| 2006/0060190 | A1 | 3/2006 | Sinderby | |
| 2006/0079793 | A1 | 4/2006 | Mann | |
| 2006/0161376 | A1 | 7/2006 | Hartlaub | |
| 2006/0167516 | A1 | 7/2006 | Kjellstrom | |
| 2006/0184154 | A1 | 8/2006 | Moberg | |
| 2006/0271029 | A1 | 11/2006 | Abboud | |
| 2006/0282040 | A1 | 12/2006 | Toman | |
| 2007/0060871 | A1 | 3/2007 | Istoc | |
| 2007/0078381 | A1 | 4/2007 | Yap | |
| 2007/0142732 | A1 | 6/2007 | Brockway | |
| 2007/0149926 | A1 | 6/2007 | Moberg | |
| 2007/0191770 | A1 | 8/2007 | Moberg | |
| 2007/0232936 | A1 | 10/2007 | Mann | |
| 2007/0244469 | A1 | 10/2007 | Ozeri | |
| 2007/0258083 | A1 | 11/2007 | Heppell | |
| 2007/0270782 | A1 | 11/2007 | Miesel | |
| 2007/0274843 | A1 | 11/2007 | Vanderveen | |
| 2008/0009837 | A1 | 1/2008 | Miesel | |
| 2008/0027349 | A1 | 1/2008 | Stylos | |
| 2008/0097287 | A1 * | 4/2008 | Nelson et al. | 604/65 |

(56) References Cited

U.S. PATENT DOCUMENTS

| | | |
|---|---|---|
| 2008/0139996 A1 | 6/2008 | Bowman |
| 2008/0167641 A1* | 7/2008 | Hansen et al. ............ 604/891.1 |
| 2008/0221522 A1 | 9/2008 | Moberg |
| 2008/0221523 A1 | 9/2008 | Moberg |
| 2009/0082757 A1* | 3/2009 | Rogers et al. ............ 604/891.1 |
| 2010/0016918 A1 | 1/2010 | Mann |
| 2010/0037680 A1 | 2/2010 | Moberg |
| 2011/0077605 A1 | 3/2011 | Karpowicz |

FOREIGN PATENT DOCUMENTS

| | | |
|---|---|---|
| EP | 0 328 162 | 8/1989 |
| EP | 0 522 527 | 12/1994 |
| EP | 0 856 326 | 8/1998 |
| EP | 0 621 791 | 8/2000 |
| EP | 1 342 481 | 9/2003 |
| EP | 1 535 637 | 6/2005 |
| EP | 0 993 268 | 11/2005 |
| EP | 1 839 695 | 10/2007 |
| EP | 1 592 468 | 9/2008 |
| WO | WO 95/32013 | 11/1995 |
| WO | WO 99/55225 | 11/1999 |
| WO | WO 00/44420 | 8/2000 |
| WO | WO 02/064040 | 8/2002 |
| WO | WO 02/070047 | 9/2002 |
| WO | WO 2005/072792 | 8/2005 |
| WO | WO 2005/089860 | 9/2005 |
| WO | WO 2005/119181 | 12/2005 |
| WO | WO 2006/067217 | 6/2006 |
| WO | WO 2006/108775 | 10/2006 |
| WO | WO 2007/020029 | 2/2007 |

OTHER PUBLICATIONS

"The SynchroMed Pump" datasheet, [online], Medtronic, Inc., Minneapolis, MN, Version b3.01, [retrieved on Oct. 19, 2007]. Retrieved from the Internet:URL:http://www.medtronic.com/neuro/paintherapies/pain_treatment_ladder/drug.infusion/pumps_pump_sel/synchromed_pumps:html; 4 pgs.
PCT Search Report and Written Opinion dated Feb. 3, 2011.
U.S. Appl. No. 12/623,484, filed Nov. 23, 2009.
U.S. Appl. No. 11/731,356, filed Mar. 30, 2007.
U.S. Appl. No. 11/731,355, filed Mar. 30, 2007.
U.S. Appl. No. 11/778,400, filed Jul. 16, 2007.

* cited by examiner

A)

B)

DETERMINING CATHETER STATUS

RELATED APPLICATIONS

This application is a continuation-in-part application of (i) application Ser. No. 12/623,484, filed on Nov. 23, 2009, (ii) application Ser. No. 11/731,356, filed on Mar. 30, 2007, which published on Oct. 2, 2008 as US 2008/0243074, (iii) application Ser. No. 11/731,355, filed on Mar. 30, 2007, published on Nov. 22, 2007 as US 2007/0270782, which claims priority to Provisional Application No. 60/789,729, filed on Apr. 6, 2006, and (iv) application Ser. No. 11/778,400, filed on Jul. 16, 2007, which published on Jan. 10, 2008 as US 2008/009837, which is a continuation of application Ser. No. 10/836,115 filed on Apr. 30, 2004, now U.S. Pat. No. 7,320,676, which claims priority to Provisional Application No. 60/508,020, filed on Oct. 2, 2003, which patents and applications are hereby incorporated herein by reference in their respective entireties to the extent that they do not conflict with the present disclosure.

FIELD

The present disclosure relates generally to systems and methods for identifying malfunctions in an implanted catheter of an infusion system by sensing fluid pressure.

BACKGROUND

Implantable infusions systems are commonly used to chronically deliver therapeutic agents to target locations of patients. For example, more than 100,000 individuals worldwide are implanted with an infusion system configured to deliver therapeutic agent to the cerebrospinal fluid (CSF) of a patient. Such systems typically have a reservoir containing a supply of therapeutic substance awaiting delivery to the patient's CSF. A pump may be fluidly coupled to the reservoir for creating fluidic pressure to facilitate delivery of the therapeutic substance. A catheter provides a pathway for delivering the therapeutic substance to the CSF of the patient. All parts of the infusion system need to operate adequately to ensure proper delivery of therapeutic substances using the system.

While perhaps the least complex component of an infusion system, catheters can have operational problems or can develop operational problems. For example, catheters may be placed in the wrong location when originally implanted or the catheters may move (migrate) over time such that fluids (e.g., therapeutic substances) delivered through the catheters are not delivered to the originally intended delivery site (e.g., a CSF compartment). Catheters can also become obstructed or clogged during use. A partial or complete blockage could prevent an adequate supply of the therapeutic substance from reaching the intended delivery site of the patient. Catheters can also leak due to cuts, tears, etc. A leak, small or large, can also prevent some or all of the therapeutic substance from reaching the selected internal delivery site of the patient and may result in therapeutic substance being delivered to unintended sites, which may create further issues.

Some infusion systems have been proposed which include pressure sensors capable of monitoring pressure in the catheter to determine whether a catheter malfunction has occurred. However, many of such systems and methods fail to provide refined information regarding the nature of the malfunction.

SUMMARY

This disclosure, among other things, describes systems and methods that allow for refined determination of catheter status of implanted infusion systems in which the catheter is intended to deliver therapeutic agent to a target region of a patient, such as the CSF. The systems and methods, in various embodiments described herein, monitor changes in catheter pressure associated with physiological parameters ("physiological pressure") and changes in catheter pressure associated with bolus infusion of fluid into the catheter or bolus withdrawal of infusion from the catheter ("bolus pressure"). As described herein, information that cannot be obtained from monitoring physiological pressure or bolus pressure alone can be obtained from combined monitoring of physiological pressure and bolus pressure.

That such additional information could be obtained has not been suggested previously. For example, US 2008/0243074, to which the present application claims priority, describes, among other things, that catheter leaks, occlusions and the like can be detected via monitoring of pressure changes in the catheter that are associated with physiological pressure changes, and 2007/0270782, to which the present application also claims priority, describes, among other things, that catheter leaks, occlusions and the like can be detected via monitoring of pressure changes in the catheter due to in bolus infusion or withdrawal. The ability to derive additional information via the combination of physiological pressure and bolus pressure monitoring is not suggested in these prior applications.

Examples of the additional information that may be derived from combined physiological pressure and bolus pressure monitoring include whether a catheter has migrated out of cerebrospinal fluid (CSF), whether a catheter has a leak within a region in a CSF compartment of a patient, and whether a delivery region of a catheter in a CSF compartment is adjacent solid tissue of a patient. Thus, monitoring of pressure changes in the lumen of the catheter in response to both physiological events (physiological pressure) and bolus infusion or withdrawal (bolus pressure) may be advantageous relative to monitoring only one of physiological pressure or bolus pressure.

In various embodiments, the present disclosure describes a method for determining whether a delivery region of an implanted catheter has migrated out of a CSF compartment. The method includes measuring pressure within a lumen of the catheter, developing a physiological pressure modulation profile based on the measured pressure, and determining whether the developed physiological pressure modulation profile is indicative of a catheter having a delivery region in the cerebrospinal fluid compartment by comparing the developed physiological pressure modulation profile to a predetermined physiological pressure profile of the cerebrospinal fluid compartment. The method further includes infusing or withdrawing a bolus of fluid into or from a lumen of the catheter. The lumen of the catheter is in communication with the delivery region. The method further includes measuring pressure within the lumen of the catheter created by the bolus, developing a bolus pressure modulation profile based on the measured bolus pressure, and determining whether the developed bolus pressure modulation profile is indicative of a catheter complication by comparing the developed bolus pressure modulation profile to a predetermined bolus pressure profile. In addition, the method includes determining that the delivery region of the catheter has migrated out of the cerebrospinal fluid compartment if (i) the developed physiological pressure modulation profile is determined not to be indicative of a catheter having a delivery region in the cerebrospinal fluid compartment, and (ii) the developed bolus pressure modulation profile is determined to not be indicative of a catheter complication. That is, if a bolus pressure profile of a catheter free from leaks or occlusions is detected, then the catheter is likely functioning normally, and therefore, has likely migrated, explaining the failure to detect the characteristic CSF physiological pressure profile. If the catheter has migrated out of the CSF, it may be possible to move the catheter back into the CSF without explanting the entire catheter.

In various embodiments, the present disclosure describes a method for determining whether a catheter having a delivery region implanted in a cerebrospinal fluid compartment has a leak within the cerebrospinal fluid compartment. The method includes measuring pressure within a lumen of the catheter, developing a physiological pressure modulation profile based on the measured pressure, and determining whether the developed physiological pressure modulation profile is indicative of a catheter having a delivery region in the cerebrospinal fluid compartment by comparing the developed physiological pressure modulation profile to a predetermined physiological pressure profile of the cerebrospinal fluid compartment. The method further includes infusing or withdrawing a bolus of fluid into or from a lumen of the catheter. The lumen of the catheter is in communication with the delivery region. The method further includes measuring pressure within the lumen of the catheter created by the bolus, developing a bolus pressure modulation profile based on the measured bolus pressure, and determining whether the developed bolus pressure modulation profile is indicative of a catheter having a leak by comparing the developed bolus pressure modulation profile to a predetermined bolus pressure profile. In addition, the method includes determining that the catheter has a leak within the cerebrospinal fluid compartment if (i) the developed physiological pressure modulation profile is determined to be indicative of a catheter having a delivery region in the cerebrospinal fluid compartment, and (ii) the developed bolus pressure modulation profile is determined to be indicative of a catheter having a leak. If the catheter has a leak in the CSF, it may be determined that the catheter need not be explanted if it is acceptable that the agent to be delivered by the catheter simply be delivered to the CSF as opposed to a particular location of the CSF. Making such a determination may save the patient an undesired surgery to explant the catheter and may save significant costs.

In various embodiments, the present disclosure describes a method for determining whether a catheter having a delivery region implanted in a cerebrospinal fluid compartment is adjacent a solid tissue. The method includes measuring pressure within a lumen of the catheter, developing a physiological pressure modulation profile based on the measured pressure; and determining whether the developed physiological pressure modulation profile is indicative of a catheter having a delivery region in the cerebrospinal fluid compartment by comparing the developed physiological pressure modulation profile to a predetermined physiological pressure profile of the cerebrospinal fluid compartment. The method further includes withdrawing a bolus of fluid from a lumen of the catheter. The lumen of the catheter is in communication with the delivery region. The method further includes measuring pressure within the lumen of the catheter created by the bolus, developing a first bolus pressure modulation profile based on the measured bolus pressure, and determining whether the developed first bolus pressure modulation profile is indicative of a catheter having an occlusion by comparing the developed first bolus pressure modulation profile to a predetermined bolus pressure profile. The method may further include infusing a bolus of fluid into the lumen of the catheter, measuring pressure in the lumen of the catheter created by the bolus, developing a second bolus pressure modulation profile based on the measured bolus pressure, and determining whether the developed second bolus pressure modulation profile is indicative of a catheter having an occlusion by comparing the developed second bolus pressure modulation profile to a predetermined bolus pressure profile. In addition, the method includes determining that the delivery region is adjacent a solid tissue if (i) the developed physiological pressure modulation profile is determined to be indicative of a catheter having a delivery region in the cerebrospinal fluid compartment, (ii) the developed first bolus pressure modulation profile is determined to be indicative of an occlusion, and (iii) the developed second bolus pressure modulation profile is not determined to be indicative of an occlusion. If the delivery region of the catheter is considered to be undesirably adjacent to solid tissue within the CSF, the delivery region may be moved by slight advancement or withdrawal of the catheter. Such information may be particularly valuable during the process of implanting the catheter so that the catheter may be optimally positioned in the patient.

In addition to the various advantages described above, other advantages of one or more embodiments of the methods and systems described herein will be apparent to those of skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
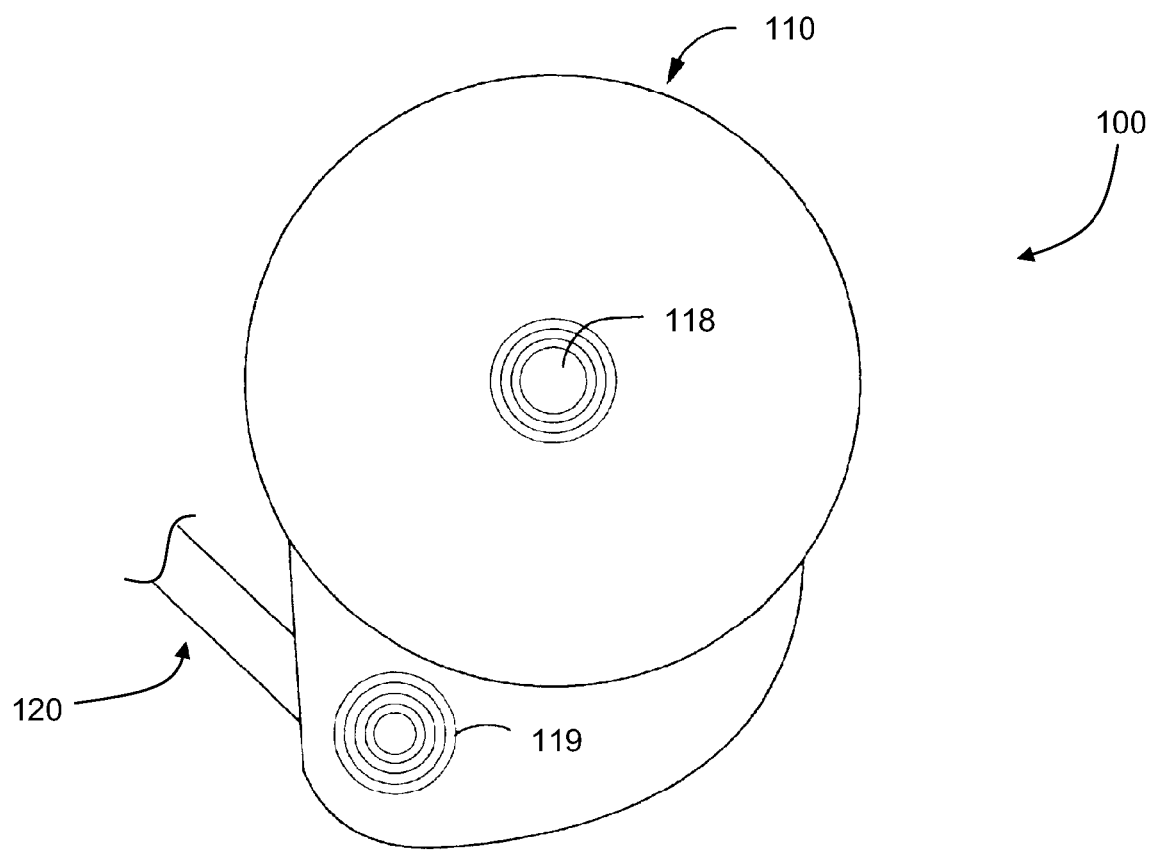
FIG. 1 is a schematic drawing of an embodiment of an implantable infusion system

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of diffe rent numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

As used herein, "implanted" with regard to a medical device, means that at least a portion of the device is placed within a subject, such as a patient. That is, for the purpose of the present disclosure, a device is implanted whether it is fully implanted or partially implanted. For example, a catheter may be considered implanted if a distal portion of the catheter has a delivery region that is located at a target region in the patient while a proximal portion of the catheter is located external to the patient.

As used herein, a "physiological pressure modulation profile" is a pressure profile that is modulated by a physiological event. For example, beating of a heart may result in pressure oscillations having a frequency and amplitude within characteristic ranges, which pressure oscillations are detectable in fluid-filled compartments of the patient, such in the vascular system or cerebrospinal fluid, and which may be transferred to a catheter having a delivery region or opening within the fluid-filled compartment. Such pressure oscillations have profiles that result from the physiological event (e.g., heart beat) and are examples of physiological pressure modulation profiles.

As used herein, a "bolus pressure modulation profile", with regard to pressure within a lumen of a catheter, is a pressure profile that is modulated by infusion or withdrawal of a bolus of fluid into or from the catheter. Characteristic pressure changes can be observed within a catheter resulting from infusion or withdrawal of a bolus of fluid through the catheter. Such pressure changes have profiles that result from the bolus and are examples of a bolus pressure modulation profiles.

As used herein, "measuring", as it relates to pressure within a lumen of a catheter, includes obtaining a single measurement, multiple measurements, periodic measurements, continuous measurements, or the like. For example, a pressure profile developed from a measured pressure may be developed from multiple pressure measurements obtained over time or pressure measurements continuously measured over time.

This disclosure, among other things, relates systems and methods that allow for refined determination of catheter status in implanted infusion systems in which the catheter is intended to deliver therapeutic agent to a target region of a patient, such as the CSF. The systems and methods, in various embodiments, monitor changes in pressure within a lumen of a catheter associated with physiological parameters ("physiological pressure") and changes in pressure within a lumen of a catheter associated with bolus infusion of fluid into the catheter or bolus withdrawal of infusion from the catheter ("bolus pressure"). As described herein, information that cannot be obtained from monitoring physiological pressure or bolus pressure alone can be obtained from combined monitoring of physiological pressure and bolus pressure.

Figure 2:
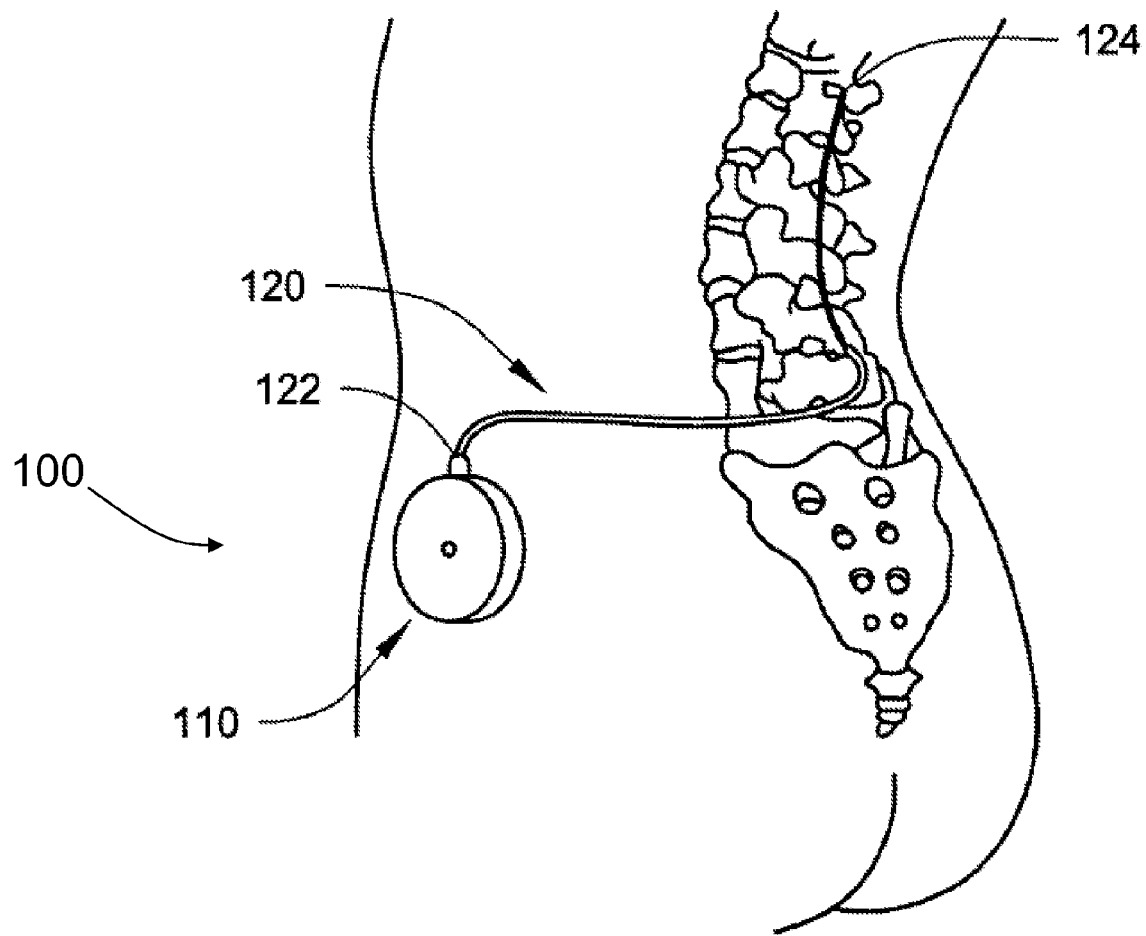
FIG. 2 is a schematic drawing depicting an embodiment of an implanted infusion device.

The methods and systems described herein may be employed with any suitable implantable infusion system. FIGS. 1-2 show examples of infusion systems 100 with which pressure monitoring systems and methods described herein may be used. The infusion system depicted in FIG. 1 includes an infusion device 110, a catheter 120, and a catheter access port 119 in fluid communication with the catheter 120. The infusion device 110 also includes a refill port 118 in communication with a reservoir for containing therapeutic agent (not shown) disposed within the housing of the device 110. The infusion device 110 may include any suitable mechanism or structure capable of delivering one or more fluids to a patient. The structures used to drive fluids in the infusion devices may be powered (e.g., piston pumps, diaphragm pumps, peristaltic pumps, etc.), may be activated based on pressure to drive fluid out of a reservoir (e.g., using collapsing diaphragms, expanding bladders, etc.), or the like. Examples of some potentially suitable pump assemblies may include, e.g., commercially available implantable infusion pumps such as, for example, the SYNCHROMED II and EL pumps, manufactured by Medtronic, Inc., Minneapolis, Minn.

The infusion system 100 depicted in FIG. 2 is shown implanted in a patient. The infusion system 100 includes an infusion device 110 and catheter 120 having a proximal end 122 attached to the infusion device 110. The infusion device 110 may be surgically implanted in any suitable location, such as subcutaneously in the pectoral, abdominal or other region of the subject's body. The distal end 124 of the catheter 120 is implanted in a patient such that the distal end 124 is located at the selected internal delivery site in the patient (in the intrathecal space of the patient as depicted in FIG. 2, the cerebroventricles, or elsewhere as desired). While not shown in FIG. 2, it will be understood that the depicted infusion device 100 may include a catheter access port in fluid communication with the catheter 120 as described above with regard to FIG. 1. The pump assembly 110 may also include a reservoir that contains a fluid (e.g., a therapeutic substance) to be infused using the system. The fluid contained within the reservoir may preferably be replenished periodically using known techniques and structures.

It will be understood that other infusion systems that be employed, such as those described in U.S. Patent Application Publication No. US 2005/0075624 A1, entitled PRESSURE SENSING IN IMPLANTABLE MEDICAL DEVICES (Miesel), which is incorporated herein by reference in its entirety to the extent that it does not conflict with the present disclosure.

An infusion system employed in accordance with the teachings presented herein may include any suitable infusion device. An infusion device may include any suitable mechanism or structure capable of delivering one or more fluids to a patient. The structures used to drive fluids in the infusion devices may be powered (e.g., piston pumps, diaphragm pumps, peristaltic pumps, etc.) or they may be activated based on pressure to drive fluid out of a reservoir (e.g., using collapsing diaphragms, expanding bladders, etc.). Examples of some potentially suitable infusion device may include, e.g., commercially available implantable infusion device such as, for example, the SYNCHROMED II and EL pumps, manufactured by Medtronic, Inc., Minneapolis, Minn.

Figure 3:
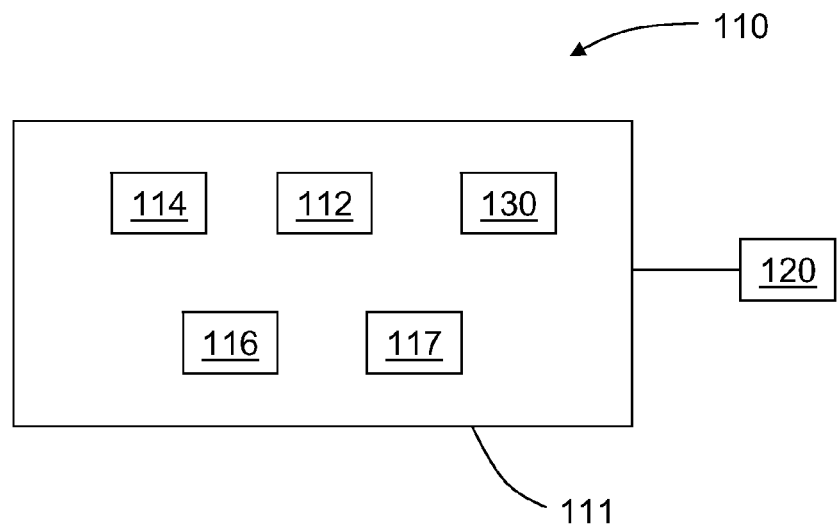
FIG. 3 is a schematic block diagram depicting an embodiment of an infusion system, showing some selected components.

Selected components of an example of an implantable infusion device 110 are depicted in FIG. 3. The depicted infusion device 110 includes a pump mechanism 112 operably coupled to a catheter 120 such that fluid within a reservoir 114 can be delivered to the catheter 120 via the pump mechanism 112. The depicted infusion device 110 includes a power supply 116 and control electronics 117 operably coupled to the power supply 116 and the pump mechanism 112 such that the infusion of fluids using the system can be controlled. Although not specifically depicted, the infusion device 110 may also include other components such as, e.g., communication devices (e.g., telemetry modules, etc.) to provide for control and/or communication between the infusion system and external devices.

In some embodiments, an implantable infusion device 110 includes a pressure sensor 130 that, in the embodiment depicted in FIG. 3, is operably coupled to the control electronics 117. The pressure sensor 130 is operably coupled to the catheter 120 in a manner that allows the pressure sensor 130 to measure the fluid pressure of fluid located within the catheter 120 and to provide a pressure signal (to, e.g., the control electronics 117) that is representative of the fluid pressure of the fluid in the catheter 120. Examples of some potentially suitable pressure sensors and their interconnection with control electronics 117 may be described in, e.g., U.S. Patent Application Publication No. US 2005/0075624 (Miesel) titled PRESSURE SENSING IN IMPLANTABLE MEDICAL DEVICES. In embodiments, where an external pressure sensor is employed (see, e.g., FIG. 5), the on-board pressure sensor 130 may be omitted from the infusion device 110.

Figure 4:
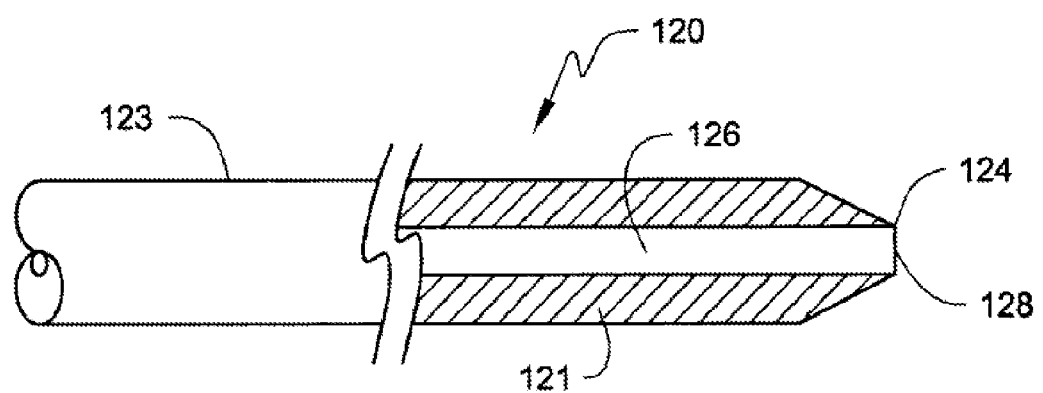
FIG. 4 is a schematic drawing of an enlarged partial cross section of an embodiment of a catheter.

FIG. 4 depicts a portion of a catheter 120 in an enlarged cross-sectional view. The catheter 120 includes an elongated tubular portion 123 that preferably extends from the proximal end (not shown) to the distal end 124. The catheter 120 depicted in FIG. 4 includes a lumen 126 that terminates at opening 128 (or delivery region) at the distal end 124. Therapeutic substances (or other fluids) delivered from the pump assembly 110 to the catheter 120 pass through lumen 126 and preferably exit the catheter 120 through opening 128.

The body of catheter 120 may be constructed of any suitable material, e.g., an elastomeric tube. Examples of some suitable materials include, but are not limited to, silicone rubber (e.g., polydimethyl siloxane) or polyurethane, both of which can provide good mechanical properties and are very flexible. Suitable materials for the catheter 120 are also preferably chemically inert such that they will not interact with therapeutic substances, body tissues, or body fluids while implanted in the patient.

Where the catheter is to be used for intrathecal fluid delivery, it may be preferred that at least a portion of the catheter 120 be sized to fit in the gap between the spinal cord and the dura within the intrathecal space. Catheters intended for delivering fluids to other internal delivery sites will be sized appropriately for those locations. As another consideration in sizing the catheter, the diameter of the lumen 126 is preferably large enough to accommodate expected infusion rates with acceptable flow resistance. The wall 121 of the catheter 120 is preferably thick enough to withstand normal handling during the implant procedure and forces from body tissues during normal motion. As an example, a catheter intended for use in intrathecal fluid delivery may have an outside diameter of 1.25 millimeters (mm), an inside diameter of 0.5 mm, and a wall thickness of 0.375 mm. Such a catheter may have a length of, e.g., 50 centimeters (cm) long to reach from, e.g., a drug infusion pump implanted in the patient's abdomen to the spine.

Although the opening 128 through which the fluid exits the catheter 120 is depicted as a simple opening in the distal end 124 of catheter 120, such an opening 128 is only one embodiment of an infusion section that may be used in connection with the teachings presented herein. Other embodiments of infusion sections may include, e.g., multiple openings, permeable membranes, or the like. Although the infusion section (opening 128) of the depicted catheter 120 is located at the distal end 124 of the catheter 120, the infusion section(s) may be positioned at any location along the length of the catheter 120 that can be used to deliver the fluid to the selected internal delivery site.

Because physiological pressure modulations at the selected internal delivery site are preferably transmitted into the fluid located within the lumens of catheters in various embodiments, the construction of the infusion sections is preferably selected to provide for that pressure transmission. In other words, the infusion sections are preferably capable of transmitting physiological pressure modulations (e.g., from the CSF where the infusion sections may be located) into the fluid located within the catheter lumen.

Figure 5:
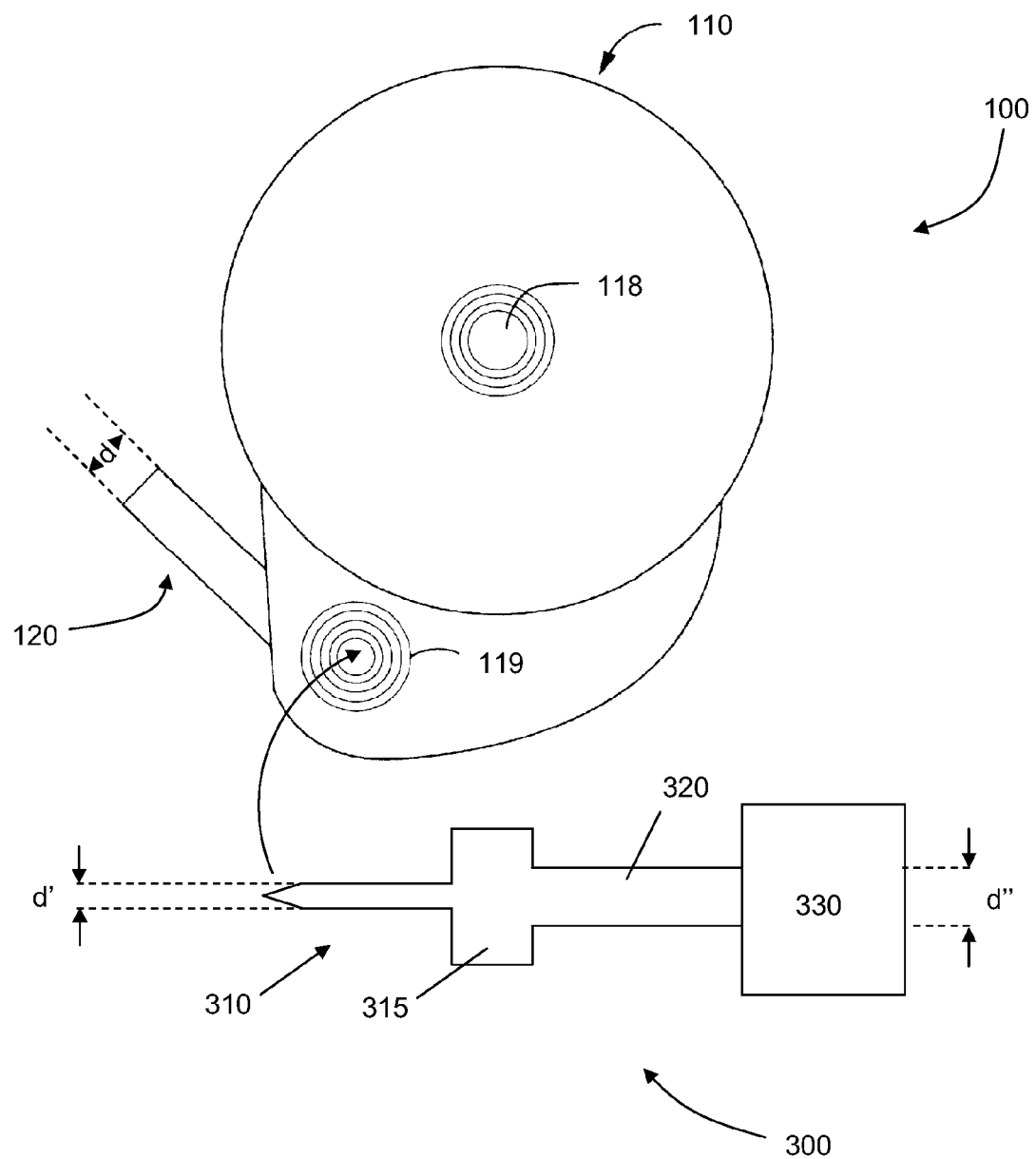
FIG. 5 is a schematic drawing of an embodiment of a pressure monitoring system and an embodiment of an implantable infusion system.

Referring now to FIG. 5, a system for external monitoring of pressure within a lumen of a catheter is shown. In the depicted embodiment, a pressure monitoring system 300 and an implantable infusion system 100 are shown. The pressure monitoring system includes a probe 310 that can be inserted transcutaneously into the catheter access port 119 of the infusion system such that a lumen of the probe 310 is placed in communication with the catheter 120. The probe 310 may contain an adaptor 315, such as a leur-type adaptor, to couple the probe to tube 320, having a lumen in communication with a pressure sensor 330. While not shown, it will be understood that the pressure sensor 330 may be coupled to connector 315 without intervening tubing 320 or may be integrated within probe 310, such as in the hub of a needle. In other words, the pressure sensor 330 may be operably coupled to the probe 310 in any suitable manner. Thus, when the probe 310 is properly inserted into the port 119, pressure changes in the catheter can be measured by the pressure sensor 330. Any suitable pressure transducer or sensor 330 may be employed.

The pressure sensor 330 may be adapted or configured to read either gauge or absolute pressure of the fluid in the lumen of the catheter 120. Because many of the methods described below rely on comparison of pressure modulation profiles, changes in ambient pressure may be of limited importance in implementing the methods because ambient pressure changes can typically be expected to exert the same influence on fluid in the catheter lumen as it does at the selected internal delivery site (e.g., on the CSF in the intrathecal space).

The probe 310 has an inner diameter d' that, in some embodiments, is less than 60% of the inner diameter d of the catheter 120 and is less than 60% of the inner diameter d" of the tube 320. Even with such changing inner diameters, pressure changes in the catheter indicative of a CSF pressure profile are capable of being detected by the external pressure sensor 330. Of course, the probe 310 may have any suitable inner or outer diameter, provided that the probe 310 may be inserted into the access port 119.

Tubing 320 may be of any suitable material, such as the materials described above with regard to the catheter. The tubing 320 may have any suitable dimensions, such as an inner diameter of about 0.5 millimeters or greater. The tubing 320 may be of any suitable length, such as a length that allows a desired distance between the probe 310 and the pressure sensor 330.

Figure 6:
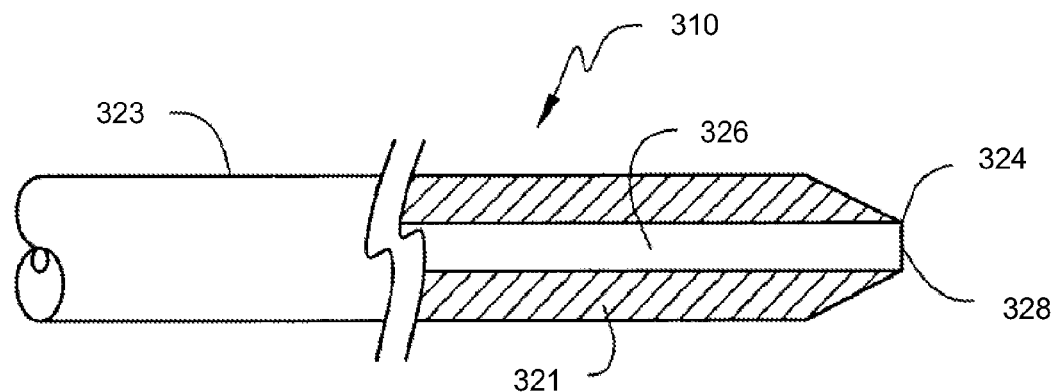
FIG. 6 is a schematic drawing of an enlarged partial cross section of an embodiment of a probe.

Referring now to FIG. 6, an enlarged partial cross-sectional view of a probe 310 is shown. The probe 310 includes an elongated tubular portion 323 that preferably extends from the proximal end (not shown) to the distal end 324. The probe 310 depicted in FIG. 6 includes a lumen 326 that terminates at opening 328 at the distal end 324. Thus, when the distal end 324 is inserted into a catheter access port, the lumen 326 of the probe 310 is placed in fluid communication with the catheter.

The body of probe 310 may be constructed of any suitable material, e.g., rigid metallic material or a rigid plastic. The material should be sufficiently stiff that is can be inserted transcutaneously into a catheter access port without compromising the integrity of the lumen. Examples of suitable materials include stainless steel and titanium. In various embodiments, the inner diameter of probe, as defined by the lumen 326, is less than 0.35 millimeters. In many embodiments, the probe is a 24-gauge or higher-gauge needle. For many catheter access ports of implantable infusion systems, needles of a gauge less than 24 gauge are too large of an outer diameter to be inserted into the port.

Figure 7:
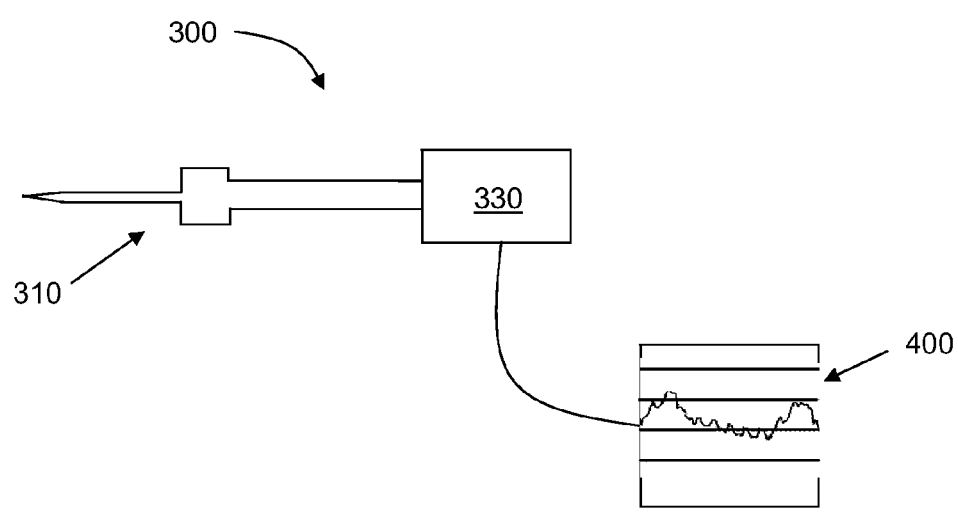
FIG. 7 is a schematic block drawing of an embodiment of a pressure monitoring system operably coupled to a monitor for displaying a pressure profile.

Referring now to FIG. 7 an external pressure monitoring system 300 may include a monitor 400 for displaying pressure profiles. The pressure profiles displayed may be pressure profiles developed from the pressure measured via pressure sensor 330, may be pressure profiles of characteristic CSF pressure profiles or bolus profiles, which are discussed in more detail below, or the like. The system may also include a processor that allows conversion of the measured pressure data into the displayed pressure profile. A possessor may also be employed to compare the developed pressure profiles to characteristic CSF or bolus profiles to assist in determining whether the profiled developed from the measured pressures have characteristics indicative or not indicative of a CSF or bolus profile.

The pressure monitoring system may also communicate with a second device via wires or wirelessly, such as via Bluetooth, USB, serial, or the like, to transmit raw or processed pressure information to the second device capable. The second device or a tertiary device operably coupled to the second device is capable of displaying the pressure information. The second device may be a physician programmer, patient programmer, computer, or the like. It will be understood that an implantable infusion device having an onboard pressure sensor and associated electronics (e.g., as depicted in FIG. 3) may also communicate, directly or indirectly, with a monitor for displaying pressure profiles.

It will also be understood that any suitable pressure monitor or pressure monitoring system may be employed to monitor pressure within the lumen of the catheter and that the systems, or components thereof, depicted in FIGS. 3 and 5-7 are just examples of pressure monitors or monitoring systems that may be employed. For additional examples of external pressure monitoring systems that may be employed, see co-pending application Ser. No. 12/623,484, filed on Nov. 23, 2009, to which the present application claims priority, may be employed. Additional details regarding onboard pressure sensors and appropriate electronics may be included in an implantable infusion device are described in, for example, US 2008/0243074 or US 2007/0270782, to which the present application claims priority.

As mentioned above, one way to determine the underlying cause of a catheter malfunction is to deliver or withdraw a bolus of fluid into or from the catheter and monitor the resulting pressure profile following the bolus. Any suitable bolus may be delivered over any suitable amount of time, provided that a characteristic profile can be measured. In some embodiments, e.g. where the implantable infusion device to which the catheter is connected includes a programmable pump, the pump may be programmed to deliver a bolus of fluid and the resulting pressure and pressure decay profile may be observed via an appropriate pressure monitoring system, such as the system depicted in FIG. 3 or FIG. 5. Alternatively, an external system having an appropriate mechanism for delivering or withdrawing a bolus of fluid through a probe that can be inserted into a catheter access port of an infusion device may be employed (see, e.g., FIG. 5). Additional details regarding examples of suitable external systems are provided in co-pending application Ser. No. 12/623,484, to which the present application claims priority. In many cases, use of an external system to deliver or withdraw the bolus may allow for greater displacement of fluid, resulting in greater pressure changes that may allow for more accurate evaluation of catheter status. Any suitable fluid, such as therapeutic fluid, water, saline, artificial cerebrospinal fluid, or the like may be delivered as the bolus.

Referring now to FIGS. 8A-B, schematic drawings showing hypothetical plots of infusion rate versus time (A) and pressure within a lumen of a catheter versus time (B) are shown. The time (x-axis) in FIGS. 8A and 8B are simultaneous. As a bolus is delivered (FIG. 8A), pressure in a properly functioning catheter transiently increases and returns to baseline following a characteristic decay profile (see curve N). In an occluded catheter (curve O), the pressure may (but does not necessarily) increase beyond the maximum pressure observed in a normally functioning catheter free from leaks or occlusions (not shown in FIG. 8B), and has a characteristically slower decay rate than a normal functioning catheter. In a catheter having a leak (curve L), the decay rate (time and profile, by which pressure returns to baseline) is characteristically faster than in a properly functioning catheter. While the maximum pressure achieved in curve L depicted in FIG. 8B is equal to the maximum pressure shown in curve N, it will be understood that in some situations a leaky catheter may exhibit a maximum pressure less than the maximum pressure observed in a normally functioning catheter free of leak or occlusions. It is notable that the differences in the profiles between occluded, leaky, and properly functioning catheters are detectable in catheters that do not have flow restrictors or valves, which are lacking in most of the currently implanted catheters that are part of an implanted infusion system. The extent of the change in profile in an occluded (O) or leaky (L) catheter relative to a properly functioning catheter (N) will vary depending on the extent of the occlusion (e.g., partial vs.

full) or leak (e.g., small vs. large). Some partial occlusions or small leaks may not be readily detectable. However, such leaks and occlusions may not be of therapeutic significance.

In addition, it will be understood that the differences in pressure profiles between occluded (O), leaky (L), and properly functioning (N) catheters will be amplified or attenuated depending on the amount of fluid introduced into the catheter in the bolus, as well as the rate the bolus is delivered to the catheter. Characteristic pressure profiles can be generated empirically, theoretically or otherwise for a given catheter of a given length with a given bolus delivered at a given rate. The rates and bolus amounts can be varied to achieve a variety of profiles that may be used to determine whether the observed profile in an implanted catheter is that of a properly functioning catheter, an occluded catheter (possible increase in maximal pressure or slower decay rate) or of a leaky catheter (possible decrease in maximal pressure and faster decay rate).

Figure 9A:
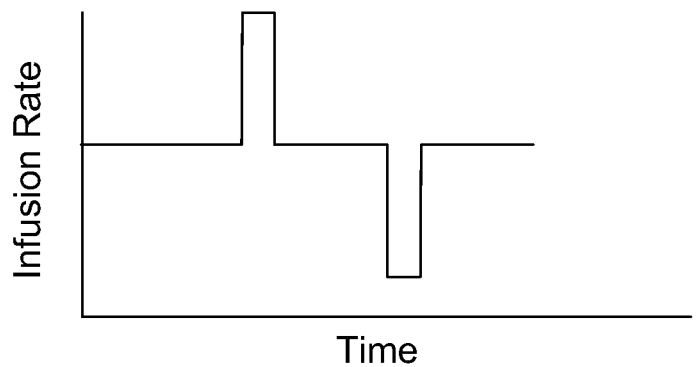
FIG. 9A is a schematic drawing of a graph of infusion rate into a catheter over time.
Figure 9B:
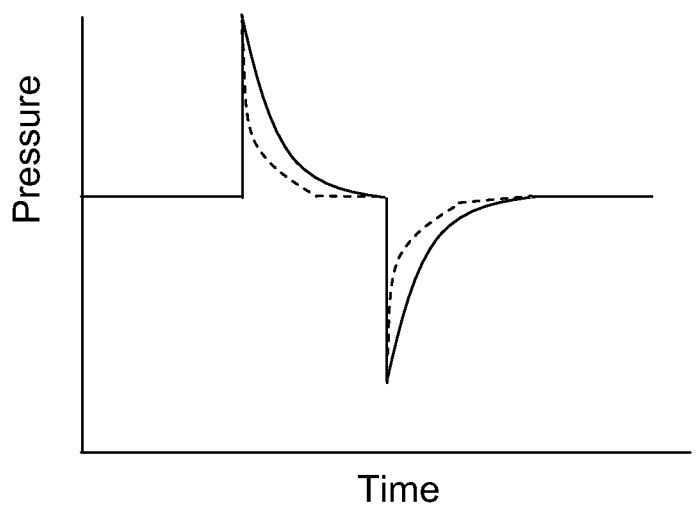
FIG. 9B is a schematic drawing of graphs of pressure within a lumen of a catheter following the infusion depicted in FIG. 9A. The curves correspond to a leaky (dashed lines), and a normally functioning (solid lines) catheter.
Figure 9C:
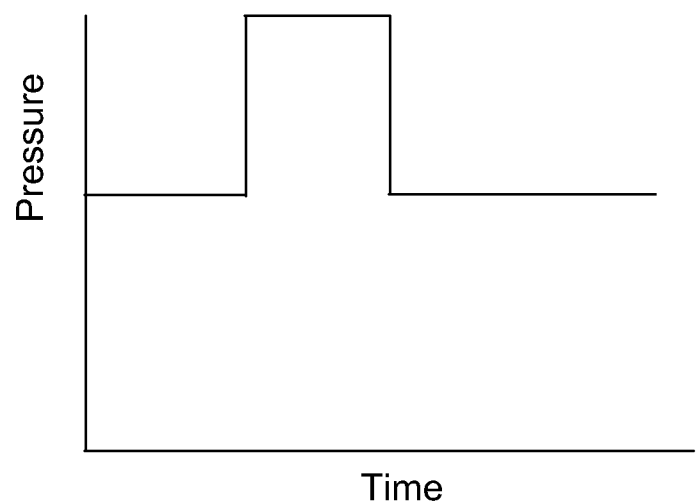
FIG. 9C is a schematic drawing of a graph of pressure within a lumen of a catheter following the infusion depicted in FIG. 9A. The curve corresponds to an occluded catheter

Referring now to FIGS. 9A-C, schematic drawings showing hypothetical plots of infusion rate versus time (A) and pressure within a lumen of a catheter versus time (B,C) are shown. The time (x-axis) in FIGS. 9A-C are simultaneous. As shown in FIG. 9A, delivery of a bolus of fluid is followed by withdrawal of a bolus of infusion (or vice-versa). Representative resulting pressure profiles for a properly function catheter (solid lines) and a leaky catheter (dashed lines) are shown in FIG. 9B. The pressure decay rate of a leaky catheter is expected to be faster than the decay rate of a non-leaky catheter. In FIG. 9C, a representative resulting pressure profile of a fully occluded catheter is shown. The pressure increases as fluid a bolus is infused into the blocked catheter until it reaches a maximum and returns to baseline upon withdrawal of the same amount of fluid that was introduced via the initial bolus.

Figure 8:
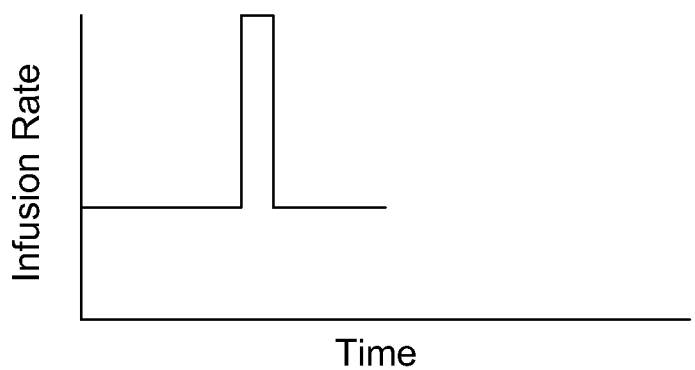
FIG. 8A is a schematic drawing of a graph of infusion rate into a catheter over time.
FIG. 8B is a schematic drawing of graphs of pressure within a lumen of a catheter following the bolus infusion depicted in FIG. 8A. The curves correspond to an occluded (O), a leaky (L), and a normally functioning (N) catheter.
Figure 8:
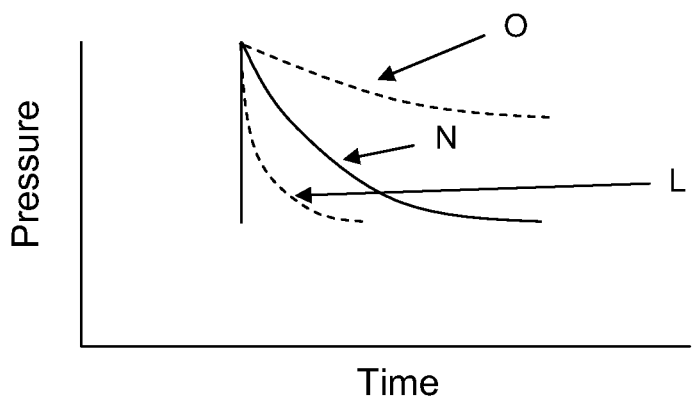

The pressure profiles depicted in FIGS. 8-9 are shown for purposes of illustration. It will be understood that the pressure profiles observed n practice may vary from those depicted. However, regardless of the profile, the characteristics of a leaky, occluded, or properly function catheter may be detected and may be transmitted via a transcutaneously inserted probe in placed communication with the implanted catheter.

As mentioned above, another way to determine the status of a catheter of an implantable infusion device is to monitor pressure within a lumen of a catheter for characteristic physiologic pressure changes of cerebral spinal fluid (CSF) in which the catheter is implanted. Examples of such methods are described in U.S. Patent Application Publication No. 2008/0243074A1, entitled CATHETER MALFUNCTION DETERMINATIONS USING PHYSIOLOGIC PRESSURE, published on Oct. 2, 2008, to which the present application claims priority.

Figure 10:
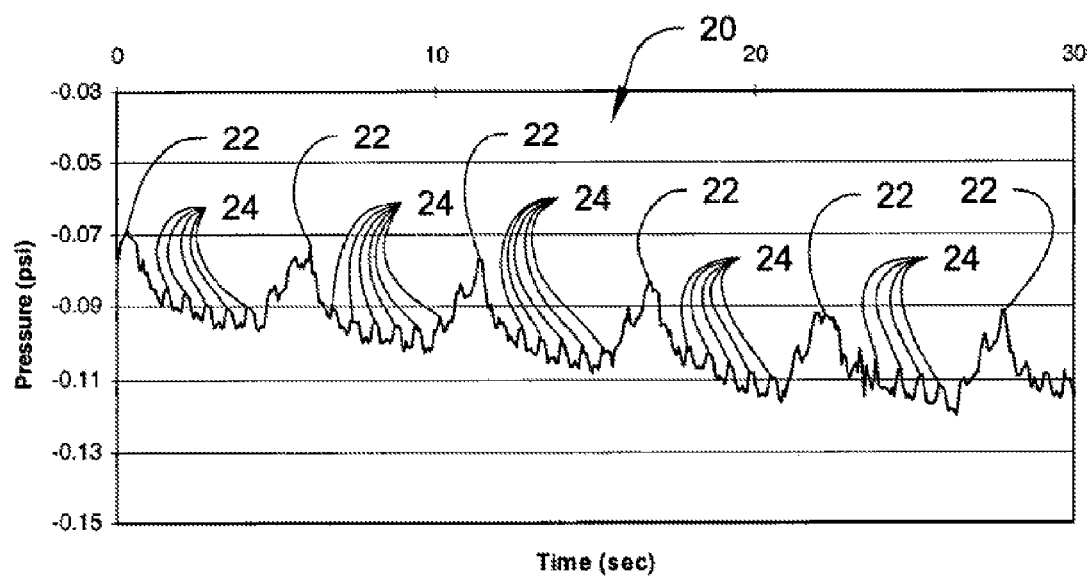
FIG. 10 is a representative graph of fluid pressure (y-axis) versus time (x-axis) in a catheter having an infusion section located in the CSF in the intrathecal space.

An example of a representative pressure profile of CSF in an animal, such as a sheep or dog, on mechanical ventilation is shown in FIG. 10. Pressure in the CSF has characteristic patterns that can be transmitted to a catheter in communication with the CSF, and thus through a probe and to an external pressure sensor (if an onboard pressure sensor is not employed). The representative data plotted in FIG. 10 demonstrates these patterns, where the plot 20 represents pressure of fluid within a lumen of a catheter located in fluid communication with the CSF. The pressure profile includes repeating major peaks 22 representative of patient respiration activity and repeating minor peaks 24 representative of cardiac activity (i.e., heartbeats). The major peaks 22 and minor peaks 24 are transmitted into the fluid in the lumen from the CSF (into which the lumen opens). The major peaks 22 repeat about every 2 to 10 seconds, which corresponds to about 30 to 6 breaths per minute. Typically, major peaks 22 repeat about every 3 to 5 seconds, which corresponds to about 20 to 12 breaths per minute. The amplitude of the major peaks 22 can vary (e.g., depending on the nature of the catheter), but are often less than 4 mmHg in amplitude, typically between about 1 mmHg and about 4 mmHg or between about 1 mmHg and 3 mmHg within a catheter such as Medtronic, Inc.'s Model 8709SC or 8731 SC silicone catheters with an inner diameter of about 0.53 mm.

The minor peaks 24 repeat about every half second to about every second and a half, which corresponds to about 40 to 120 heart beats per minute. Typically, the minor peaks 24 repeat about every 0.6 seconds to about every 1 second, corresponding to a heart rate of about 100 beats per minute to about 60 beats per minute. The amplitude of the minor peaks 24 can vary (e.g., depending on the nature of the catheter), but are often between about 0.5 mmHg and about 1 mmHg in amplitude within a catheter such as Medtronic, Inc.'s Model 8709SC or 8731SC silicone catheters with an inner diameter of about 0.53 mm.

It should be noted that the pressure associated with respiration is exaggerated in cases where an animal is on mechanical ventilation (e.g, as shown in FIG. 10) relative to a free-breathing animal. Accordingly, the differences in amplitude of the peaks corresponding to respiration (major peaks) and heart rate (minor peaks) may not be as discernable in a free-breathing animal or human. It will be understood pressure changes that generally repeat in coordination with the animal's or patient's breathing or heart rate may be detected, regardless of the amplitude. In some instances, it may be difficult to detect pressure changes associated with both breathing and heart rate. However, pressure changes in the CSF or other fluid filled compartment associated with one or the other of heart rate and respiration are typically detectable and are transmittable via a catheter having an infusion section opening into the compartment. In some embodiments, characteristic pressure changes associated with one or both of heart rate and respiration are detected to determine catheter status.

Although physiological pressure modulations may be caused by respiration or cardiac activity at the selected internal delivery site, other physiological pressure modulations may be caused by, e.g., changes in posture. For example, as a patient moves from a horizontal (e.g., supine, prone, etc.) position to an upright position, the spinal column of a human moves from a generally horizontal orientation to a generally vertical orientation. In response to such posture changes, the fluid head of the CSF within the intrathecal space will change. Fluid-head pressure modulations caused by posture changes will typically be greater towards the lower end of the spinal column due to the larger volume of CSF located above the lower end of the spinal column when the spinal column is generally vertical. Such physiological pressure modulations may be controlled by directing a patient to change posture and measuring/detecting the resulting pressure modulations.

Other physiologic parameters that can result in a CSF pressure change that can be detected via a pressure monitoring system as described herein include pressure changes due to a patient coughing or performing a valsalva maneuver (forceable exhalation against a closed airway that can be done by closing one's mouth and pinching one's nose shut).

Figure 11:
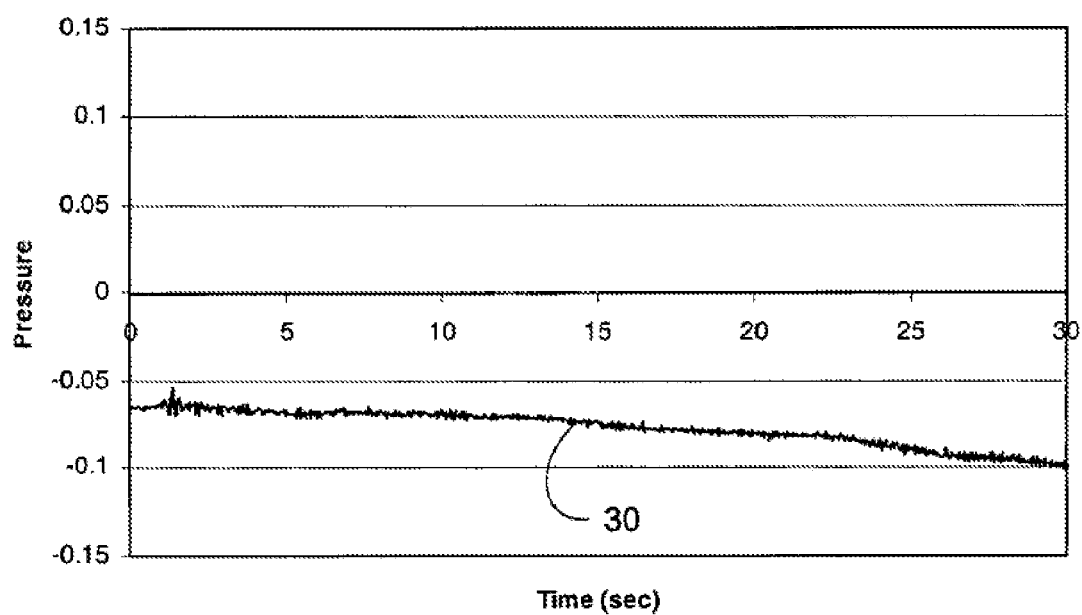
FIG. 11 is a graph of fluid pressure (y-axis) versus time (x-axis) in a catheter having an infusion section located outside the CSF.

Referring now to FIG. 11, a representative physiological pressure profile of a catheter having a delivery region located outside the CSF in a non-fluid compartment of an animal is shown. As depicted in FIG. 11, representative physiological pressures are not detected within catheters located in non-fluid filled compartments, such as the CSF.

Figure 12:
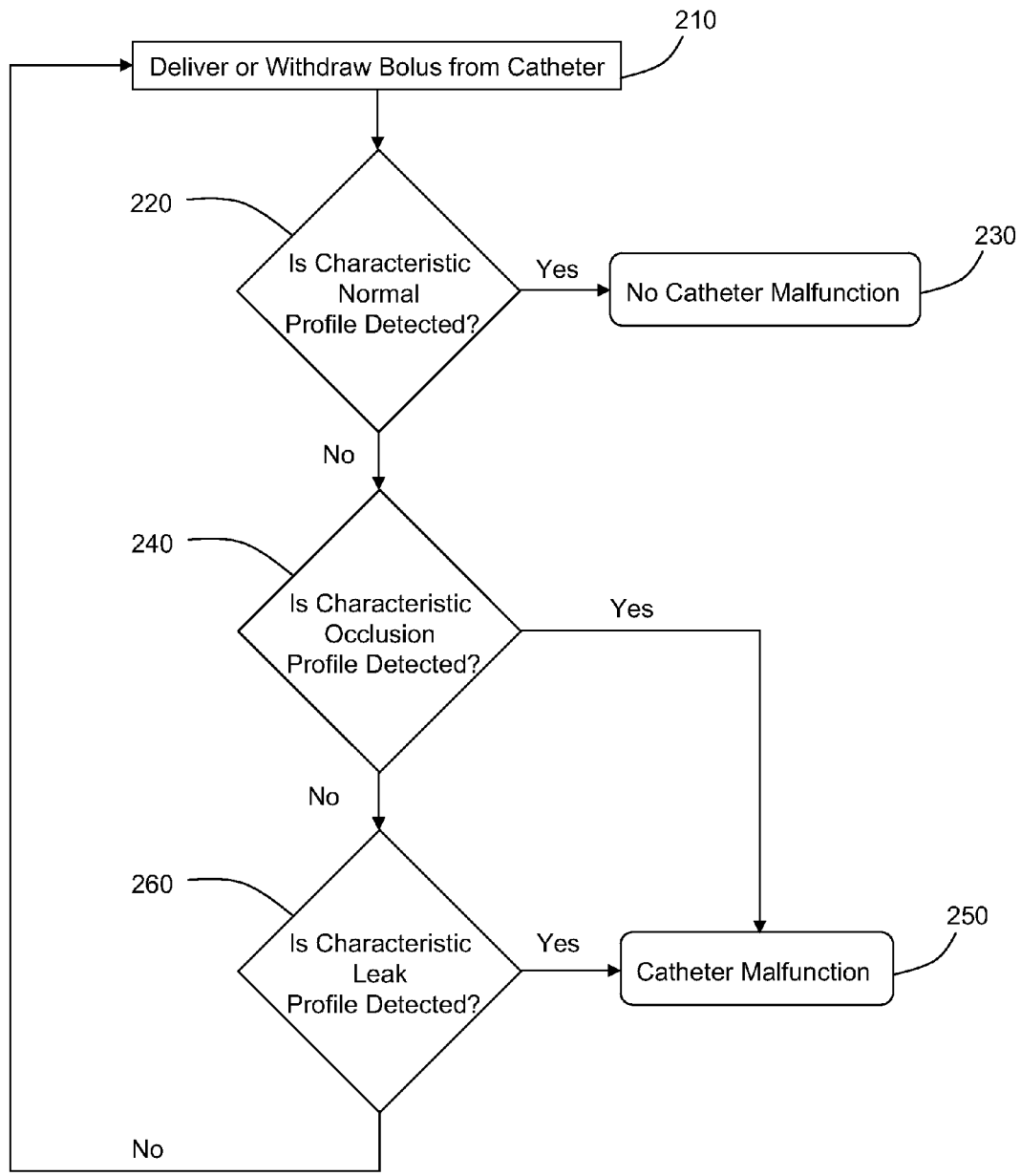
FIGS. 12-17 are flow diagram providing overviews of embodiments of methods described herein.

Referring now to FIG. 12 an overview of an aspect that may be employed with methods in accordance with various embodiments of the disclosure is depicted. The depicted aspect includes delivering or withdrawing a bolus of fluid from a catheter of an implantable infusion system (210) and monitoring bolus pressure profiles associated with the bolus (220, 240, 260). Methods describing use of such bolus pressure profiles to determine whether a catheter complication may exist are described in, for example, co-pending patent application Ser. No. 12/623,484 and US patent application publication no. 2007/0270782, to which the present application claims priority. The bolus may be delivered by the implantable infusion device to which the catheter is connected or may be delivered (or withdrawn) via an external system (e.g., as described in co-pending application Ser. No. 12/623,484). The resulting pressure within a lumen of a catheter may be monitored via a pressure sensor (onboard an infusion device or external) to determine whether a pressure profile characteristic of a properly functioning catheter (220), an occluded catheter (240), or a catheter having an unintended leak (260) is observed or detected. If a pressure profile characteristic of a properly functioning catheter is observed or detected (220), a determination that no catheter malfunction exists can be made (230). If a pressure profile characteristic of an occluded catheter (240) or a leaky catheter (260) is observed or detected, a determination that a catheter malfunction exists can be made (250). If the results are inconclusive, the process or a portion thereof may be repeated. Further, and as described in more detail below, the information obtainable from a method as depicted in FIG. 12, by itself, may not always be complete or conclusive.

Figure 13:
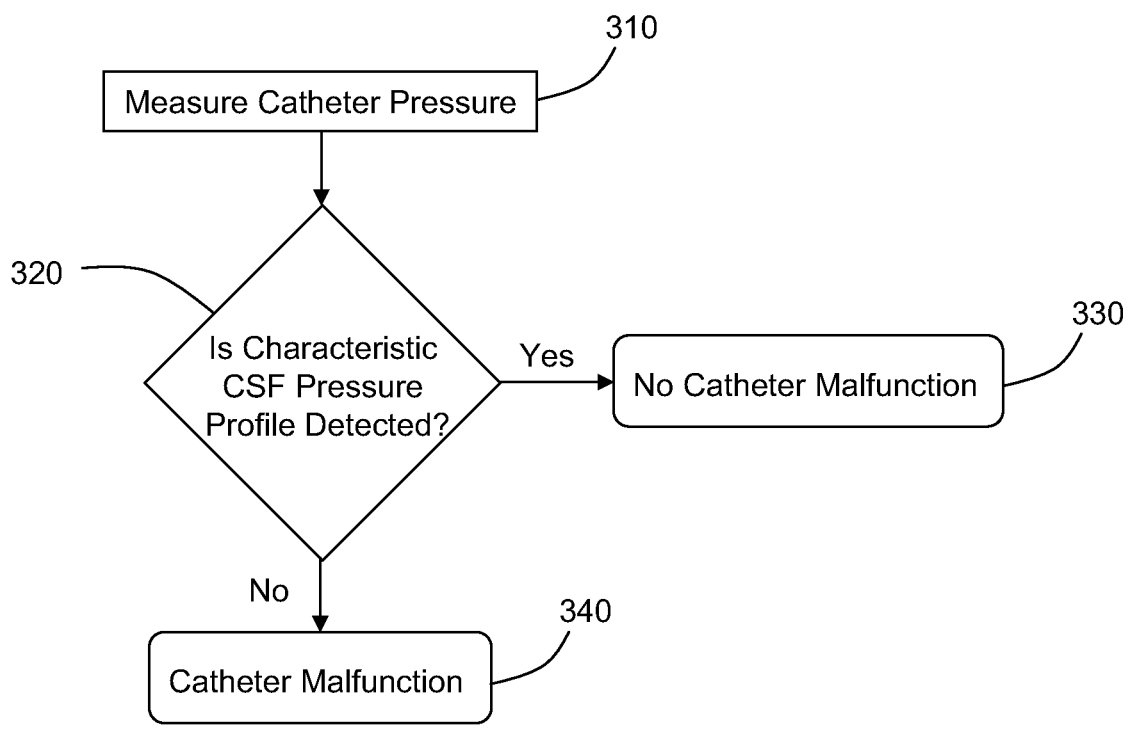

Referring now to FIG. 13 an overview of an aspect that may be employed with methods in accordance with various embodiments of the disclosure is depicted. The depicted aspect includes measuring pressure within a lumen of a catheter via a pressure sensor operably coupled to the lumen of the catheter (310). A pressure profile may be developed based on the measured pressure and a determination can be made as to whether the pressure profile is characteristic of a CSF pressure profile (e.g., as shown in, and discussed with regard to FIG. 10, as produced by a posture change, a cough, a valsalva maneuver, or the like). Methods describing use of such physiological pressure profiles to determine whether a catheter complication may exist are described in, for example, co-pending patent application Ser. No. 12/623,484 and US patent application publication no. 2008/0243074, to which the present application claims priority. If the developed profile based on the measured pressure is characteristic of a CSF pressure profile, a determination may be made that the catheter is functioning properly (320). However, as described in more detail below, the information obtainable from a method as depicted in FIG. 12, by itself, may not always be complete or conclusive.

Figure 14:
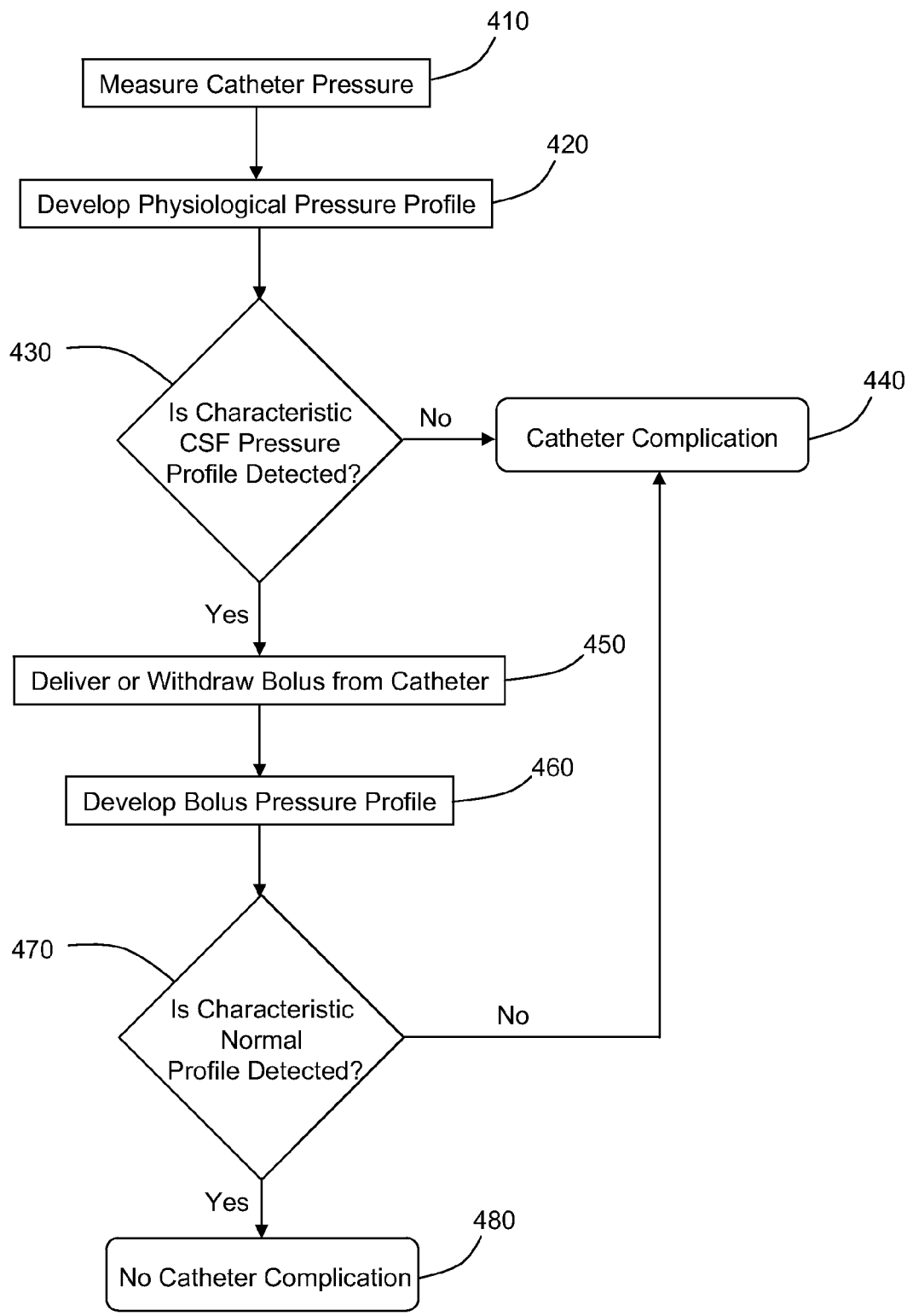
Figure 15:
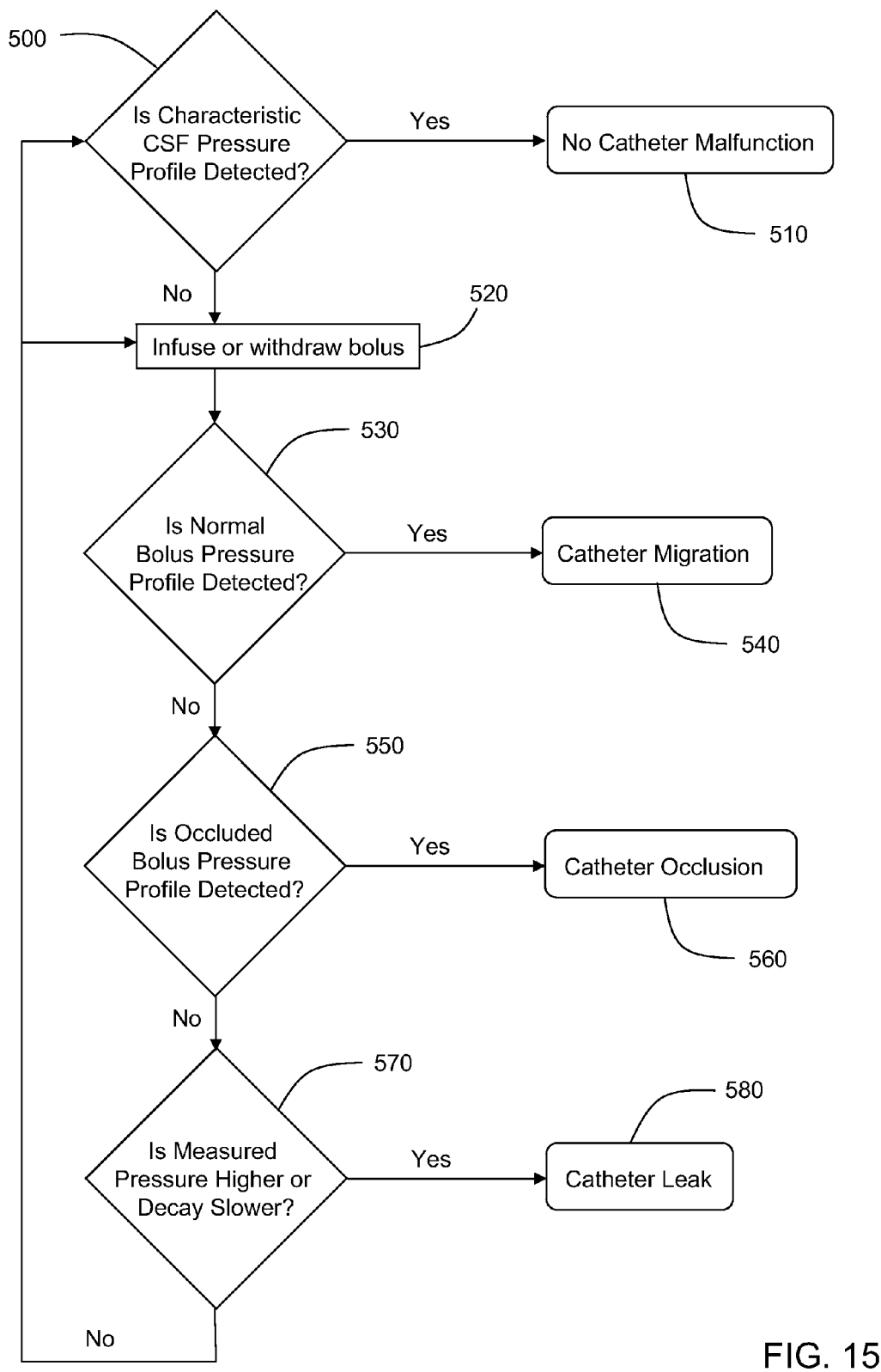
Figure 16:
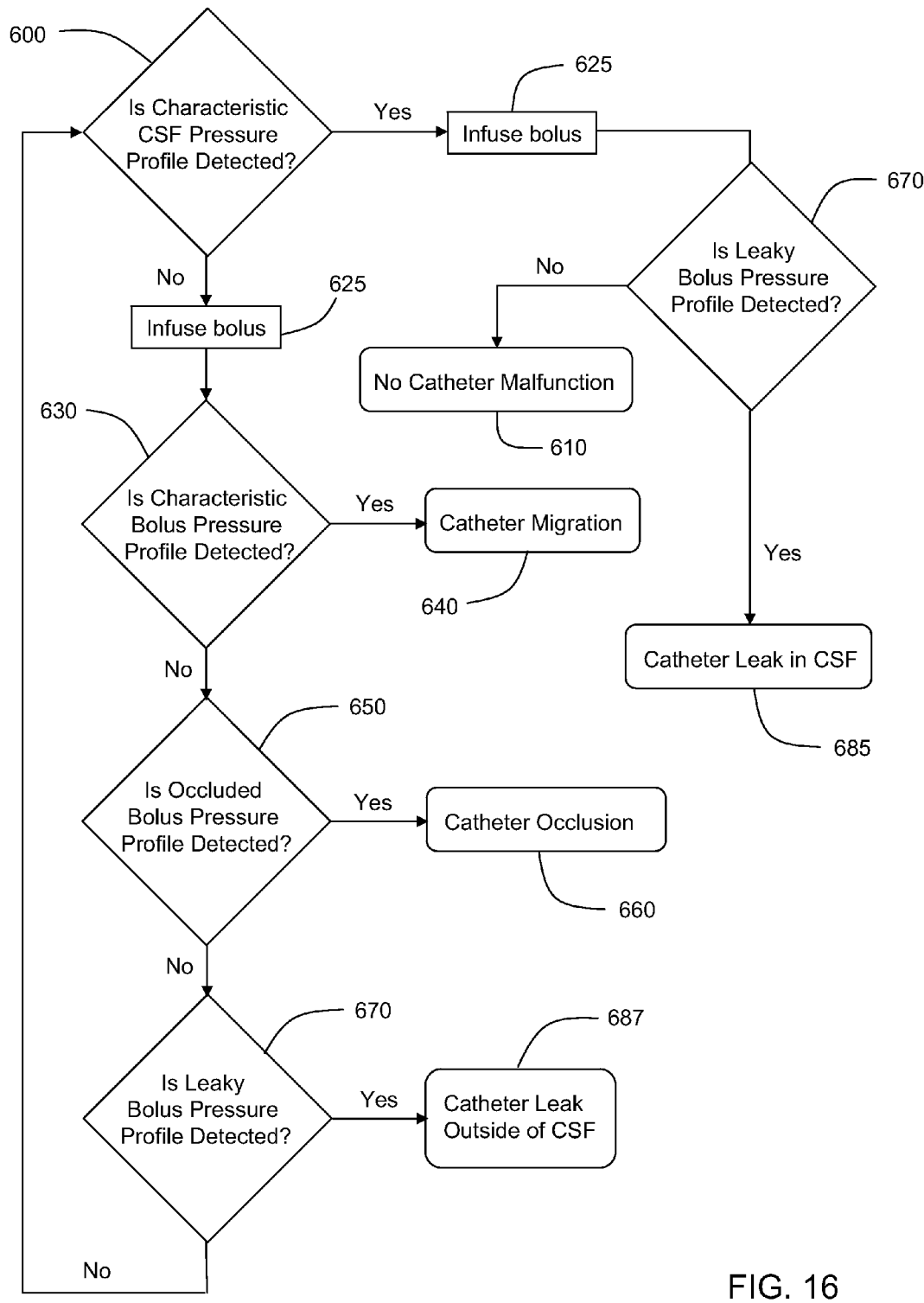
Figure 17:
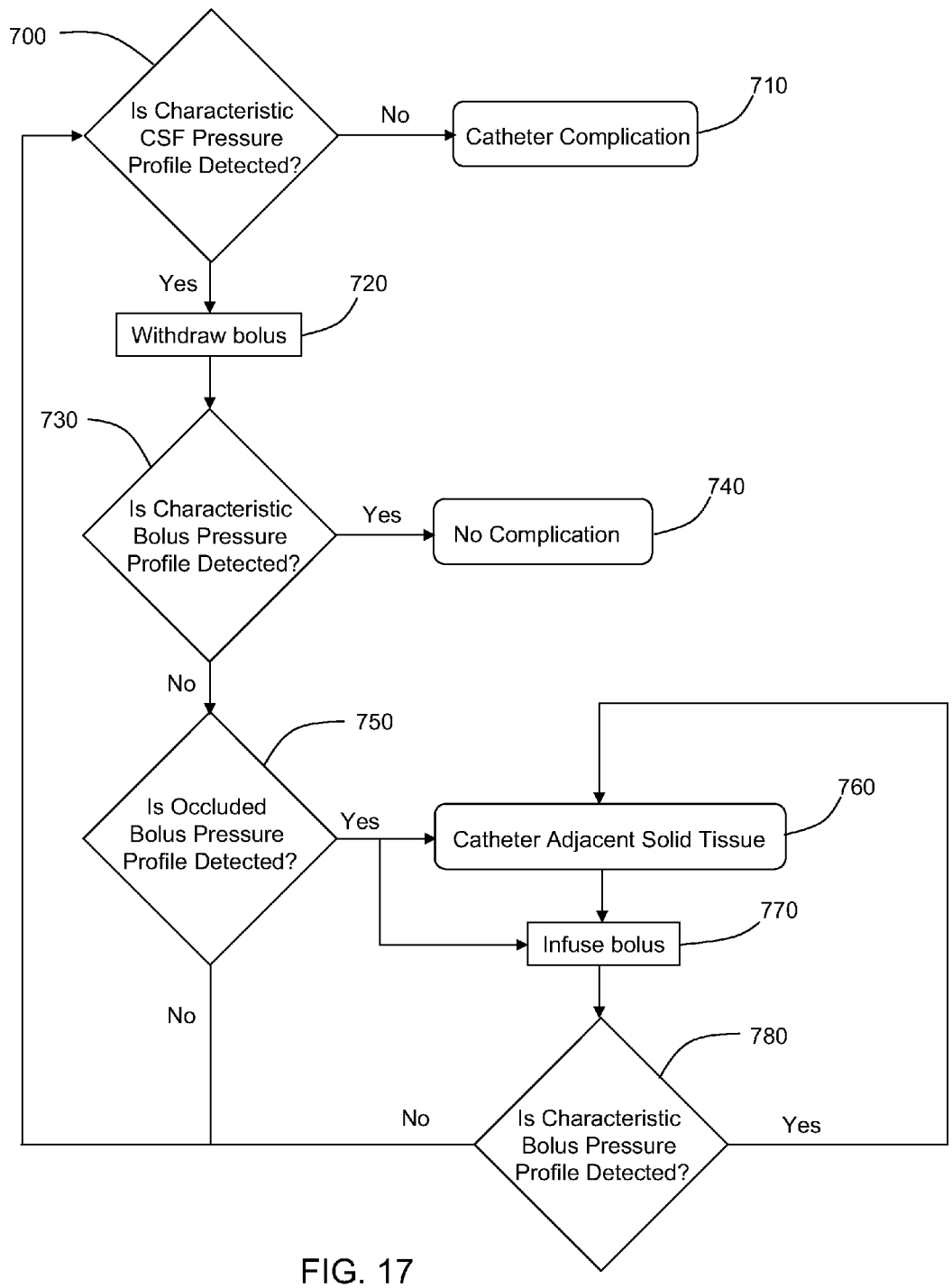

Referring now to FIGS. 14-17, overviews of various methods that combine monitoring of physiological pressure changes (e.g. as shown in FIGS. 10-11) and bolus pressure changes (e.g. as shown in FIGS. 8-9) are shown. An overview of a general method is depicted in FIG. 14, and examples of methods that illustrate additional information that can be gained by the combination that cannot be derived from either physiological pressure changes or bolus pressure changes alone are shown in FIGS. 15-17.

As shown in FIG. 14, a method may include measuring pressure within a lumen of a catheter (410), developing a physiological pressure modulation profile based on the measured pressure (420), and determining whether the developed physiological pressure modulation profile is indicative of a catheter having a delivery region placed in the CSF (430). The determination (430) may be made by comparing the developed physiological pressure modulation profile to a predetermined physiological pressure modulation profile. If it is determined that the developed pressure modulation profile is not indicative of a catheter having a delivery region in the CSF, a catheter complication may exist (440). The method further includes infusing or withdrawing a bolus of fluid into or from the catheter (450), developing a bolus pressure modulation profile based on measured pressure associated with delivery or withdrawal of the bolus (460), and determining whether the developed bolus pressure modulation profile is indicative of a properly functioning catheter (470). The determination (470) may be made by comparing the developed physiological pressure modulation profile to a predetermined bolus pressure modulation profile. If it is determined that the developed pressure modulation profile is not indicative of a properly functioning catheter, a catheter complication may exist (440). If the physiological pressure modulation profile is indicative of a catheter having a delivery region in the CSF and the bolus modulation profile is indicative of a properly functioning catheter, the catheter may be free of complications (480). In some embodiments, if a determination is made that only one of (i) the physiological pressure profile is not indicative of a catheter having a delivery region in the CSF, or (ii) the bolus pressure profile is not indicative of a properly functioning catheter, then further analysis is performed to obtain additional information regarding the status of the catheter complication or malfunction (e.g., as described below with regard to FIGS. 15-17).

Referring now to FIGS. 15-17, the depicted methods provide additional information regarding the cause of the catheter malfunction or complication. For example, and referring to FIG. 15, if a catheter malfunction is determined to exist because a characteristic CSF pressure profile is not detected (500), which detection may be carried out as described with regard to FIG. 13, a bolus of fluid may be infused into (or withdrawn from) the catheter (520). If a bolus pressure profile characteristic of a properly functioning catheter (see, e.g., curve N in FIG. 8) is detected (530), a determination can be made that the catheter (or at least the infusion section) has migrated out of the CSF (540). Such a determination could not be made with either the physiologic pressure profile or the infusion profile alone. If a bolus pressure profile characteristic of an occluded catheter (see, e.g., curve O in FIG. 8) is detected (550), a determination can be made that the catheter is occluded (360). If a bolus pressure profile characteristic of a catheter having a leak (see, e.g., curve L in FIG. 8) is detected (570), a determination can be made that the catheter has a leak (580). The measured bolus pressure profile may be compared to an occluded profile empirically, theoretically, or otherwise generated, a leaky profile empirically, theoretically, or otherwise generated, or may be compared to a profile of properly functioning catheter to determine whether there is a shift in maximal pressure or decay rate indicative of a leak or occlusion. If the comparison is inconclusive as to whether the bolus profile is characteristic of a properly functioning catheter (550), an occluded catheter (540), or a leaky catheter (570), the process may be repeated from the point of infusing the bolus (520) or determining whether a characteristic CSF pressure profile can be detected (500).

Referring now to FIG. 16, it may be desirable to determine whether the catheter has a leak if a characteristic CSF pressure profile is detected (600). In such cases, the catheter may be delivering therapeutic agent to an undesired or unintended CSF region, such as the incorrect spinal level. In some situations, e.g., where the therapeutic agent is intended to be delivered broadly via the CSF, it may not be important it the therapeutic agent is being administered to a region of the CSF other than the intended region. However, in some instances, it may be desirable to know from a viewpoint of therapeutic efficacy or toxicity to know such information. As shown in FIG. 16, a bolus of fluid may be infused into (or withdrawn from) the catheter (625) following (or before or after) detection of a characteristic CSF pressure profile (600). If a bolus pressure profile characteristic of a catheter having a leak is detected or determined to exist (670), a conclusion may be made that the catheter has a leak that is within the CSF (685). Otherwise, a conclusion may be made that the catheter is placed in the CSF and functioning properly (610). On a similar note, if no characteristic CSF pressure profile is detected (600) and a leaky bolus pressure profile is detected (670), a conclusion may be made that the catheter has a leak at a location outside the CSF (687).

Referring now to FIG. 17, a method for determining whether a catheter having a delivery region in the CSF is adjacent a solid tissue is shown. The method includes determining whether a characteristic CSF profile is detected (700), which may be done as described with regard to, e.g., FIG. 13. If a characteristic CSF profile is not detected, then a catheter complication exists (710) and a method as described in FIG. 15 may be carried out to determine the nature of the complication. If a characteristic CSF profile is detected, a bolus of fluid may be withdrawn from the catheter (720) and a determination may be made as to whether a bolus pressure profile characteristic of a properly functioning catheter is detected (730). If a bolus pressure profile characteristic of a properly functioning catheter is detected, the catheter may be properly functioning and free of complications (740). If a bolus pressure profile characteristic of a properly functioning catheter is detected and the pressure within the lumen of the catheter is determined to exhibit an occluded profile (750), a determination may be made that the delivery region of the catheter is adjacent to solid tissue (760). The occluded pressure profile may result from tissue in proximity to the delivery region being sucked against the delivery region and causing resistance to the withdrawal of the bolus. If desired, a bolus of fluid may be infused into the catheter (770) to verify that the catheter is not occluded, but rather adjacent to solid tissue. If a bolus pressure profile characteristic of a properly functioning catheter is detected (780) following infusion of the bolus (770), a determination that the delivery region of the catheter is adjacent solid tissue (760) may be made. Such a method may be particularly valuable during a process of implanting the catheter to verify that the catheter is optimally positioned. Of course, such information may also be valuable once the catheter is permanently implanted.

While much of the description provided above related to monitoring pressure changes in the CSF due to physiologic parameters, it will be understood that many similar pressure changes can be observed in other fluid filled compartments of a patient, such as a patient's vasculature. Accordingly, the teachings present herein may be readily applied to monitoring pressure changes within a lumen of a catheter due to physiological parameters, where the catheter has an opening in the patient's vascular system. Determinations as to whether an occlusion or leak exists in a catheter having a delivery region implanted in a patient's artery, vein or the like may be performed in a manner similar to that described above with regard to a catheter having a delivery region implanted in the CSF.

Further, it will be understood that the bolus pressure profiles as described herein (e.g., as described with regard to FIGS. 8-9) can be effectively monitored regardless of where the catheter is intended to deliver fluid. That is, such bolus pressure profiles can be detected in catheters having a delivery region implanted in the patient's CSF, vasculature, solid tissue, or at any other location in the patient.

Whether a characteristic pressure profile following delivery or withdrawal of a bolus or associated with a physiological parameter is used to determine the status of an implanted catheter, characteristic pressure patterns, shapes, or profiles may be used to identify catheter malfunctions. Physiological pressure modulation profiles may be developed based on monitored pressure and compared to predetermined pressure profiles, such as predetermined bolus pressure profiles or predetermined physiologic profiles, for determining the status of the catheter. Predetermined pressure profiles may be generated based on empirical measurements within an individual, a group of individuals or populations. The predetermined profiles may be averaged within or between individuals or groups. The predetermined profiles may be generated based on pressure measured within a fluid filled compartment, such as the CSF, within a catheter opening into the fluid filled compartment, or the like. In some embodiments, predetermined pressure profiles are generated, at least in part, on theoretical considerations. For example, a pattern with rising and falling pressures repeating every two to ten seconds in conjunction with a patient's breathing pattern can be considered a predetermined pressure profile correlating to respiration without any empirical data. Predetermined pressure profiles for bolus delivery and withdrawal may likewise be determined based on known compliance and resistance of a given catheter or catheter type, by empirical test within a patient or sample of patients, by bench test characterization, or by purely theoretical considerations. The pressure measurements in FIGS. 8-11 depict pressure measurements as a function of time to illustrate the principles described herein. It should be understood that these pressure curves are presented as non-limiting examples. Although scales may be included, the systems and methods described herein are not limited to catheters in which these same pressures are developed. Rather, the profiles, shapes or patterns of the pressure curves may be used to identify catheter malfunctions in connection with the methods and systems presented herein.

Depending on the characteristic pressure profile monitored, the methods described herein may involve a variety of different analyses. Potential analytical methods may include, e.g., direct observation of the pressure modulation profile (e.g., on a display), comparison of the pressure modulation profile to a selected pressure profile (using, e.g., a look-up table, etc.), etc. In some methods, the physiological events that impact or modulate the physiologic pressure profile may be tracked and correlated to changes in the physiological pressure modulation profile (e.g., heart rate may be monitored, respiration may be monitored (using, e.g., thoracic impedance, etc.). In some embodiments, analytical methods to measure, for example, p-p amplitude in frequency band of interest may be used.

In various embodiments, computer-readable medium may contain instructions that cause an implantable infusion device to carry out one or more steps of the methods described herein, particularly where the infusion device has an onboard pressure sensor. In such cases, a device including the computer readable medium would have appropriate electronics for carrying out the instructions.

If it is determined that a catheter malfunction or complication as described herein exists, a variety of actions may be taken. For example, the delivery of fluid through the catheter may be terminated, the rate of delivery of the fluid may be changed, etc. In addition to, or in place of, terminating or changing the fluid delivery rate, other actions may be taken, particularly if an implanted pressure sensor is employed. For example, an alert may be provided to the patient and/or a third party (caregiver, medical personnel, etc.). The alert may be provided locally in the form of an audible signal (e.g., a buzzer), visual signal (e.g., a light), tactile signal (e.g., vibrations), etc. The alert may, in some embodiments be transmitted from the infusion system to another device, e.g., personal computer, wireless computer/telephone network, modem, etc.

While most of the discussion presented above was with regard to determining the status of a catheter in an implantable infusion system, it will be understood that the teachings presented herein may be readily applied to other systems employing implanted catheters. By way of example, the status of a catheter of a shunt system may be monitored in accordance with the teachings presented herein. The delivery region of a catheter of a shunt system, for purposes of the present disclosure, is an opening of the catheter intended to be placed in CSF of a patient. The opening is in communication with a lumen of the catheter that is configured to carry the shunted CSF. Many shunt systems include a catheter positioned in a cerebral ventricle with a port implanted in or near the skull. The port is in fluid communication with the catheter, and thus with the CSF of the ventricle.

Those skilled in the art will recognize that the preferred embodiments may be altered or amended without departing from the true spirit and scope of the disclosure, as defined in the accompanying claims.

What is claimed is:

1. A method for determining status of an implanted catheter, the catheter having a delivery region intended to be positioned in a target location of a patient, the delivery region being in communication with a lumen of the catheter, the method comprising:
    measuring pressure within the lumen of the catheter;
    developing a physiological pressure modulation profile based on the measured pressure;
    infusing or withdrawing a bolus of fluid into or from the lumen of the catheter;
    measuring pressure within the lumen of the catheter created by the bolus;
    developing a bolus pressure modulation profile based on the measured bolus pressure; and
    determining the status of the catheter by comparing the developed bolus pressure modulation profile to a predetermined bolus pressure profile and by comparing the developed physiological pressure modulation profile to a predetermined physiological pressure profile of the target location.

2. The method of claim 1, further comprising (i) determining whether the developed bolus pressure modulation profile is indicative of a catheter complication, and (ii) determining whether the developed physiological pressure modulation profile is indicative of a catheter complication.

3. The method of claim 2, wherein the target location is a cerebrospinal fluid compartment and wherein the method further comprises:
    determining that the delivery region of the catheter has migrated out of the cerebrospinal fluid compartment if (i) the developed physiological pressure modulation profile is determined to be indicative of a catheter complication, and (ii) the developed bolus pressure modulation profile is determined to not be indicative of a catheter complication.

4. The method of claim 2, wherein the target location is a cerebrospinal fluid compartment and wherein the method further comprises:
    determining that the catheter has a leak within the cerebrospinal fluid compartment if (i) the developed physiological pressure modulation profile is determined not to be indicative of a catheter complication, and (ii) the developed bolus pressure modulation profile is determined to be indicative of a catheter complication, wherein the catheter complication is determined to be a leak based on the developed bolus pressure modulation profile.

5. The method of claim 1, wherein the developed bolus pressure modulation profile is based on withdrawal of a bolus from the catheter.

6. The method of claim 5, further comprising determining that the delivery region is adjacent a solid tissue if the developed bolus pressure modulation profile is indicative of an occlusion.

7. The method of claim 6, further comprising developing a second bolus pressure modulation profile based on infusion of a bolus into the catheter, and determining whether the developed second bolus pressure modulation profile is indicative of an occlusion.

8. The method of claim 7, further comprising supporting the determination that the delivery region is adjacent a solid tissue if the developed second bolus pressure modulation profile is not indicative of an occlusion.

9. The method of claim 2, further comprising providing an alert if one or both of the developed physiological pressure modulation profile and the developed bolus pressure modulation profile are determined to be indicative of a catheter complication.

10. The method of claim 1, wherein each step of the method is carried out via an implantable infusion device operably coupled to the catheter.

11. A computer readable medium comprising instructions that cause an implantable infusion device to carry out the method of claim 1.

12. An implantable infusion device comprising the computer readable medium of claim 11 and configured to carry out the instructions.

13. The method of claim 1, wherein comparing the developed physiological pressure modulation profile to the predetermined physiological pressure modulation profile comprises determining whether the developed physiological pressure modulation profile has characteristics associated with patient respiration or heartbeat.

* * * * *